US012758697B2

(12) United States Patent
Bozzay

(10) Patent No.: US 12,758,697 B2
(45) Date of Patent: Oct. 13, 2026

(54) TRAUMA PATIENT HEMORRHAGE CONTROL INCLUDING RAPID AUTOTRANSFUSION

(71) Applicant: Lazarus Technologies LLC, Nolensville, TN (US)

(72) Inventor: Tom Bozzay, Little Rock, AR (US)

(73) Assignee: Lazarus Technologies LLC, Nolensville, TN (US)

( * ) Notice: Subject to any disclaimer, the term of this patent is extended or adjusted under 35 U.S.C. 154(b) by 0 days.

(21) Appl. No.: 19/544,999

(22) Filed: Feb. 19, 2026

(65) Prior Publication Data

US 2026/0207834 A1 Jul. 23, 2026

Related U.S. Application Data

(63) Continuation of application No. 19/190,495, filed on Apr. 25, 2025, now Pat. No. 12,576,198, which is a
(Continued)

(51) Int. Cl.
*A61M 1/36* (2006.01)
*A61M 1/02* (2006.01)
(Continued)

(52) U.S. Cl.
CPC ........ *A61M 1/3603* (2014.02); *A61M 1/0281* (2013.01); *A61M 1/1603* (2014.02);
(Continued)

(58) Field of Classification Search
CPC .............. A61M 1/3603; A61M 1/1603; A61M 1/3612; A61M 1/0281; A61M 1/1698;
(Continued)

(56) References Cited

U.S. PATENT DOCUMENTS 8,187,214 B2 * 5/2012 Brieske .............. A61M 1/3666
604/4.01
12,447,177 B2 10/2025 Dunham et al.
(Continued)

FOREIGN PATENT DOCUMENTS

WO 2022040376 2/2022

OTHER PUBLICATIONS

"U.S. Appl. No. 19/190,495, Corrected Notice of Allowability mailed Dec. 17, 2025", 2 pgs.
(Continued)

*Primary Examiner* — Philip R Wiest
(74) *Attorney, Agent, or Firm* — Schwegman, Lundberg & Woessner, P.A.

(57) ABSTRACT

A method for onsite hemorrhage control in trauma patients using a portable rapid autotransfusion device can involve recovering a first portion of patient blood from an extravascular space into a fluid reservoir of the device. A negative internal pressure can be applied to the blood. The blood can be conditioned, such as by oxygenating and removing carbon dioxide. The conditioned blood can be returned to the patient intravenously at a rate that matches the rate of blood recovery, ensuring that the net volume of returned blood is maintained substantially equal to the net volume of removed blood.

18 Claims, 15 Drawing Sheets

Related U.S. Application Data continuation-in-part of application No. 18/673,116, filed on May 23, 2024, which is a continuation-in-part of application No. PCT/US2023/035517, filed on Oct. 19, 2023.

(60) Provisional application No. 63/417,574, filed on Oct. 19, 2022.

(51) Int. Cl.
*A61M 1/16* (2006.01)
*A61M 39/22* (2006.01)

(52) U.S. Cl.
CPC ........ *A61M 1/1698* (2013.01); *A61M 1/3612* (2014.02); *A61M 1/3627* (2013.01); *A61M 39/22* (2013.01); *A61M 2202/0014* (2013.01); *A61M 2202/0021* (2013.01); *A61M 2202/0208* (2013.01); *A61M 2202/0225* (2013.01); *A61M 2202/0413* (2013.01); *A61M 2205/10* (2013.01); *A61M 2205/3303* (2013.01); *A61M 2205/3327* (2013.01); *A61M 2205/3334* (2013.01); *A61M 2205/3344* (2013.01); *A61M 2205/3368* (2013.01); *A61M 2205/36* (2013.01); *A61M 2205/50* (2013.01); *A61M 2205/7536* (2013.01); *A61M 2230/005* (2013.01); *A61M 2230/20* (2013.01)

(58) Field of Classification Search
CPC ................ A61M 1/3627; A61M 39/22; A61M 2202/0014; A61M 2202/0021; A61M 2202/0208; A61M 2202/0225; A61M 2202/0413; A61M 2250/3327; A61M 2250/3334
See application file for complete search history.

(56) References Cited

U.S. PATENT DOCUMENTS

| | | | | |
|---|---|---|---|---|
| 12,576,198 | B2 * | 3/2026 | Bozzay | A61M 1/3603 |
| 2017/0021080 | A1 * | 1/2017 | Bonczar | A61G 12/008 |
| 2017/0102846 | A1 * | 4/2017 | Ebler | A61M 1/14 |
| 2017/0246375 | A1 * | 8/2017 | Spearman | A61M 1/14 |
| 2019/0175813 | A1 | 6/2019 | Spearman | |

OTHER PUBLICATIONS

"U.S. Appl. No. 19/190,495, Notice of Allowance mailed Nov. 19, 2025", 10 pgs.
"U.S. Appl. No. 18/648,021, Notice of Allowance mailed May 5, 2026", 12 pgs.
"U.S. Appl. No. 18/673,116, Non Final Office Action mailed May 20, 2026", 10 pgs.

* cited by examiner

TRAUMA PATIENT HEMORRHAGE CONTROL INCLUDING RAPID AUTOTRANSFUSION

CLAIM OF PRIORITY

This application is a continuation of and claims the benefit of priority under 35 U.S.C. § 120 to U.S. patent application Ser. No. 19/190,495, filed on Apr. 25, 2025, which is a continuation-in-part of U.S. application Ser. No. 18/673,116 filed on May 23, 2024, which claims priority to and the benefit of U.S. Provisional Application Ser. No. 63/417,574 filed on Oct. 19, 2022 and PCT Application Serial No. PCT/US2023/035517 filed on Oct. 19, 2023, each of which is hereby incorporated herein by reference, and the benefit of priority of each of which is claimed herein.

BACKGROUND

Severe blood loss of a trauma patient can cause irreversible damage to vital organs that can lead to morbidity or death. Replacement of lost tissue fluid with plasma, blood, or other extracellular fluid can be performed to maintain the patient's blood pressure. Generally, a trauma treatment protocol can involve rapid transportation of the patient to a hospital setting for fluid resuscitation, blood transfusion, or surgical control of bleeding. Once the patient has lost a significant amount of tissue fluid, prevention of hemorrhagic shock can become a primary concern.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Figure 1A:
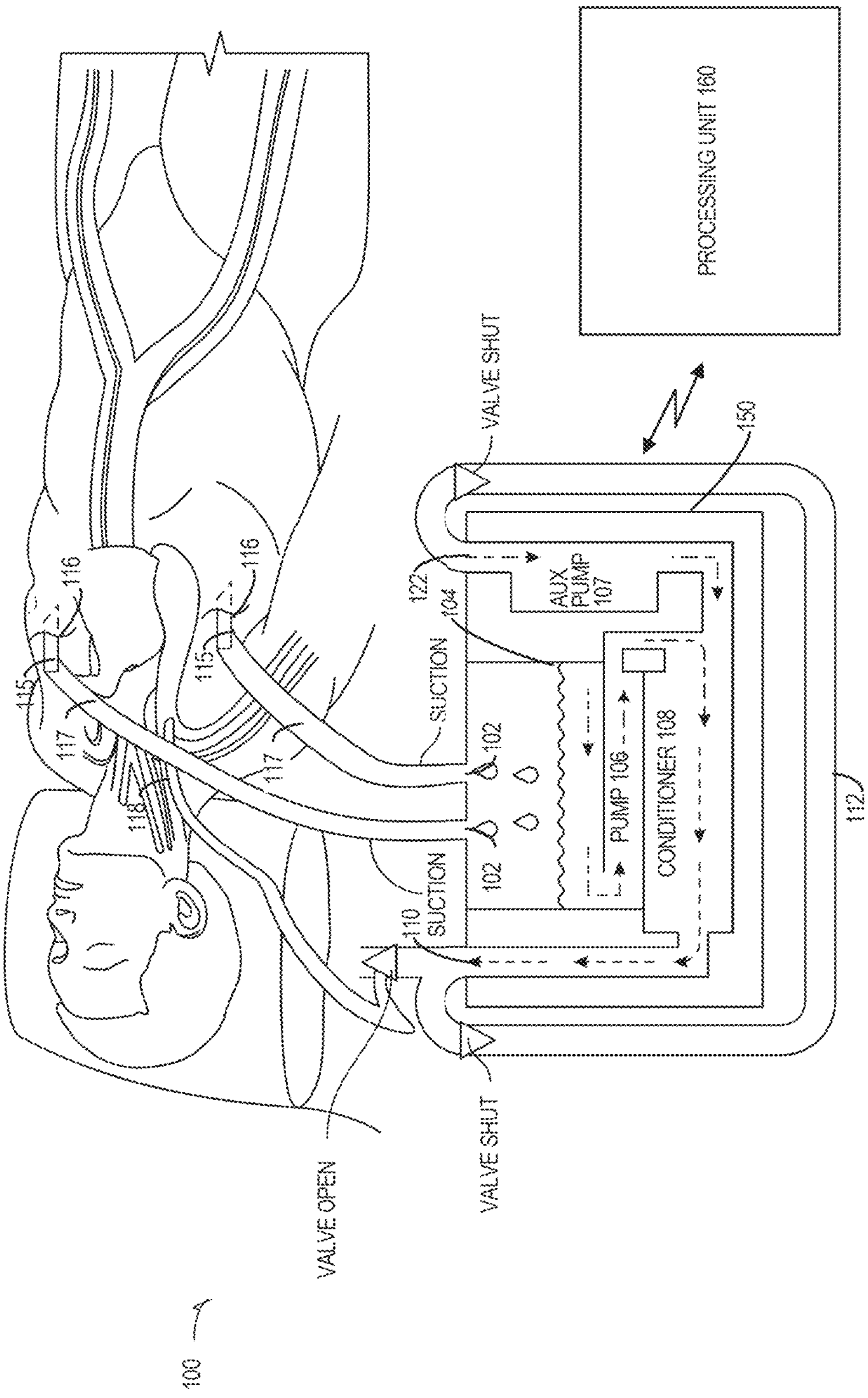
FIG. 1A depicts an example of a system for performing extracorporeal blood treatment of blood recovered from a subject.

This document relates to treatment of a trauma victim, and more specifically, blood treatment to mitigate coagulopathy, hypothermia, or acidosis of the trauma patient. Generally, hemorrhagic shock is a common cause of death among trauma patients. This condition occurs when severe blood loss leads to inadequate tissue perfusion, causing a decrease in oxygen and nutrient delivery to vital organs. As a result, the body enters a state of shock and can quickly lead to multi-organ failure and death. In severe trauma cases, such as from a gunshot wound or motor vehicle accident, the body can quickly lose a significant amount of blood volume, complicating the body's ability to maintain normal blood function.

Coagulopathy, hypothermia, and acidosis are interrelated factors that can lead to hemorrhagic shock. Coagulopathy is an imbalance between the body's pro-coagulant pathway, responsible for clot formation at the injury site, and the mechanisms that inhibit clotting away from the injury site. As the body loses blood in a trauma situation, blood flow is decreased causing hypoperfusion. Hypoperfusion results in a simultaneous lack of clotting factor replacement at the wound site (hemorrhage) and an increase in clotting in the extremities (thrombosis), both of which can cause damage to extremities and organs. Trauma Induced Coagulopathy (TIC), is an impairment of hemostasis and activation of fibrinolysis that occurs early after injury and is biochemically evident prior to, and independent of, the development of significant acidosis, hypothermia, or hemodilution. The risk of TIC increases with hypotension, higher injury severity score, worsening base deficit, and head injury. In addition, impaired liver function due to shock can also contribute to coagulopathy as the liver is responsible for producing many of the clotting factors. Hypothermia is a decrease in body temperature, which can also result from blood loss, and can further impair the body's ability to maintain normal blood function. Acidosis, referring to an abnormal increase in acidity in the body, can also result from inadequate tissue perfusion and impair the body's ability to regulate blood function. These three conditions can exacerbate one another, creating a positive feedback loop leading to severe shock and eventually death if not promptly addressed. For example, disseminated intravascular coagulation (DIC) is a systemic process producing a consumptive coagulopathy in concert with diffuse microvascular thrombosis. DIC can increase acidosis through the production of lactic acid and can also worsen hypothermia by impairing blood flow to vital organs. Hypothermia can further worsen coagulopathy, since enzymes and proteins for forming clots become less active and less effective at lower temperatures. Acidosis can also contribute to coagulopathy since the body's normal clotting processes are disrupted and become less effective at lower pH levels. Also, acidosis can further decrease body temperature, exacerbating the effects of hypothermia.

One approach to mitigating these factors and improving outcomes for trauma patients is to administer blood components, such as plasma, platelets, or red blood cells in an attempt to provide nutrients and support for the body to maintain blood functions. Such treatment involves early and aggressive treatment of a trauma patient in an attempt to restore and maintain adequate blood volume until the patient can undergo surgery or other recovery procedure. This approach can be challenging, as such treatment alone may not sufficiently address coagulopathy, hypothermia, and acidosis, particularly in severe trauma cases. For example, administering large amounts of blood products can further contribute to coagulopathy or lead to additional complications, such as fluid overload. Additionally, the use of blood products can be limited by availability, time constraints, or potential incompatibilities. Even the largest healthcare facilities can quickly become depleted of blood units in response to a large crisis, e.g., resulting from terrorism, violent crime, or natural disaster. Such crises can result in preventable deaths due to blood shortages or a lack of sufficient resources to treat the large number of trauma patients requiring immediate medical attention.

Another approach for improving outcomes for trauma patients involves administering clotting agents, such as tranexamic acid or a similar agent, to help minimize bleeding and promote clot formation. As a result, clotting agents alone will not sufficiently mitigate coagulopathy to prevent progression to severe shock but worsen shock if given at an inappropriate time. However, clotting agents at the inappropriate time can worsen coagulopathy, such as the location of the clotting. Appropriate timing for clot formation after repairing injured vessels is paramount following injury. Due to the consumptive nature of DIC, the patient's injury site where repaired vessels and grafts are sewn into place leads to poor clotting because these suture sites usually are larger vessels (higher blood flow) and micro clotting in the smaller vessels due to hypoperfusion (lower blood flow) causing decreased oxygen to the tissue and furthering acidosis. Clotting agents do not address hypothermia and acidosis, which can further impair the body's normal clotting processes.

The present inventor has recognized a need for a technique to treat or preserve a trauma patient without relying on ideal or preferred treatment conditions, e.g., availability of externally sourced blood components or rapid transportation of the patient to a large medical facility. Further, the present inventor has recognized a blood treatment technique for intervening in an initial blood treatment protocol, such as limiting tissue damage of a patient rapidly approaching hemorrhagic shock. Such an intervention can help delay the onset of cell death (necrosis) in trauma patients with a declining condition, such as providing the patient with more time to receive definitive medical treatment. A method for trauma management can include drawing blood from a body cavity, such as an intrathoracic or intra-abdominal area, of a subject via a fluid inlet of a blood treatment device. The drawn blood can be received within the device's reservoir and pumped toward an extracorporeal blood conditioner. For example, the extracorporeal blood conditioner can include an oxygenator for reoxygenating hemoglobin (Hb) or removing carbon dioxide CO2 included in the blood received from the reservoir. Also, the extracorporeal blood conditioner can include a blood temperature regulator for controlling the temperature of the blood received from the reservoir. The treated blood from at least one extracorporeal blood conditioner can be administered back to the subject, such as to help replace lost blood volume in the subject. For example, the treated blood can be intravenously administered back to the subject via the subject's internal jugular vein. An indication of a blood parameter such as volume of received blood, blood lactate, or arterial blood gas (ABG) can be monitored, and at least one operating parameter of the extracorporeal blood conditioner can be established or adjusted based on the indication. For example, the device can regulate oxygenation, flow rate, or blood temperature according to different operating modes, and an individual operating mode can be selected based on the medical condition of a subject. In operation and use, an anticoagulant can be administered to induce an anti-clotting state, and the device can be operated according to a series of modes, each mode progressively corresponding with a declining subject's medical condition. Thus, such a blood treatment technique can help monitor and inhibit coagulopathy (at least via the anticoagulant), acidosis (at least via the oxygenator), and hypothermia (at least via the blood temperature regulator) of the subject and, therefore, reduce hemorrhagic shock.

Figure 1B:
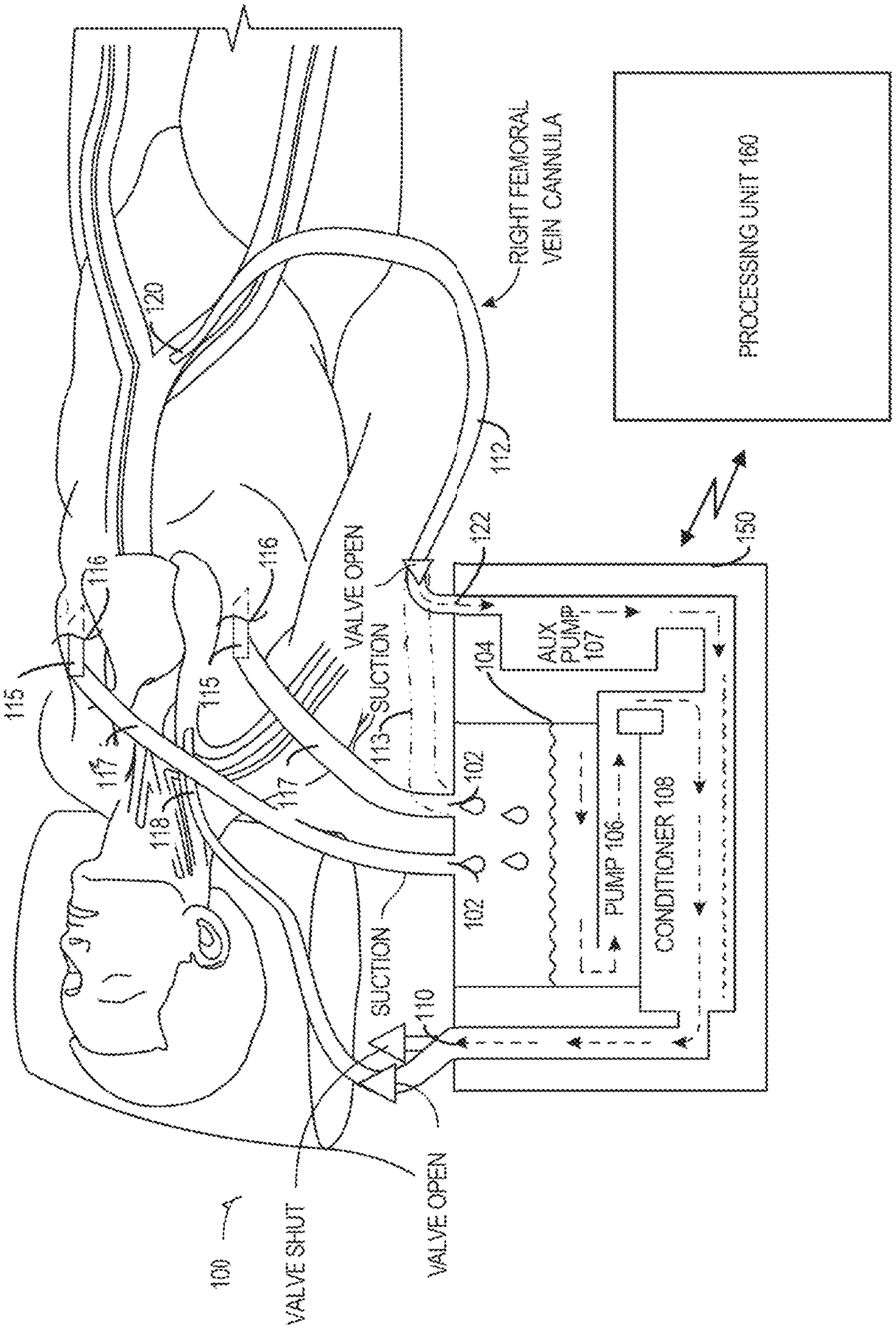
FIG. 1B depicts an example of a system for performing extracorporeal blood treatment of blood recovered from a subject.
Figure 1C:
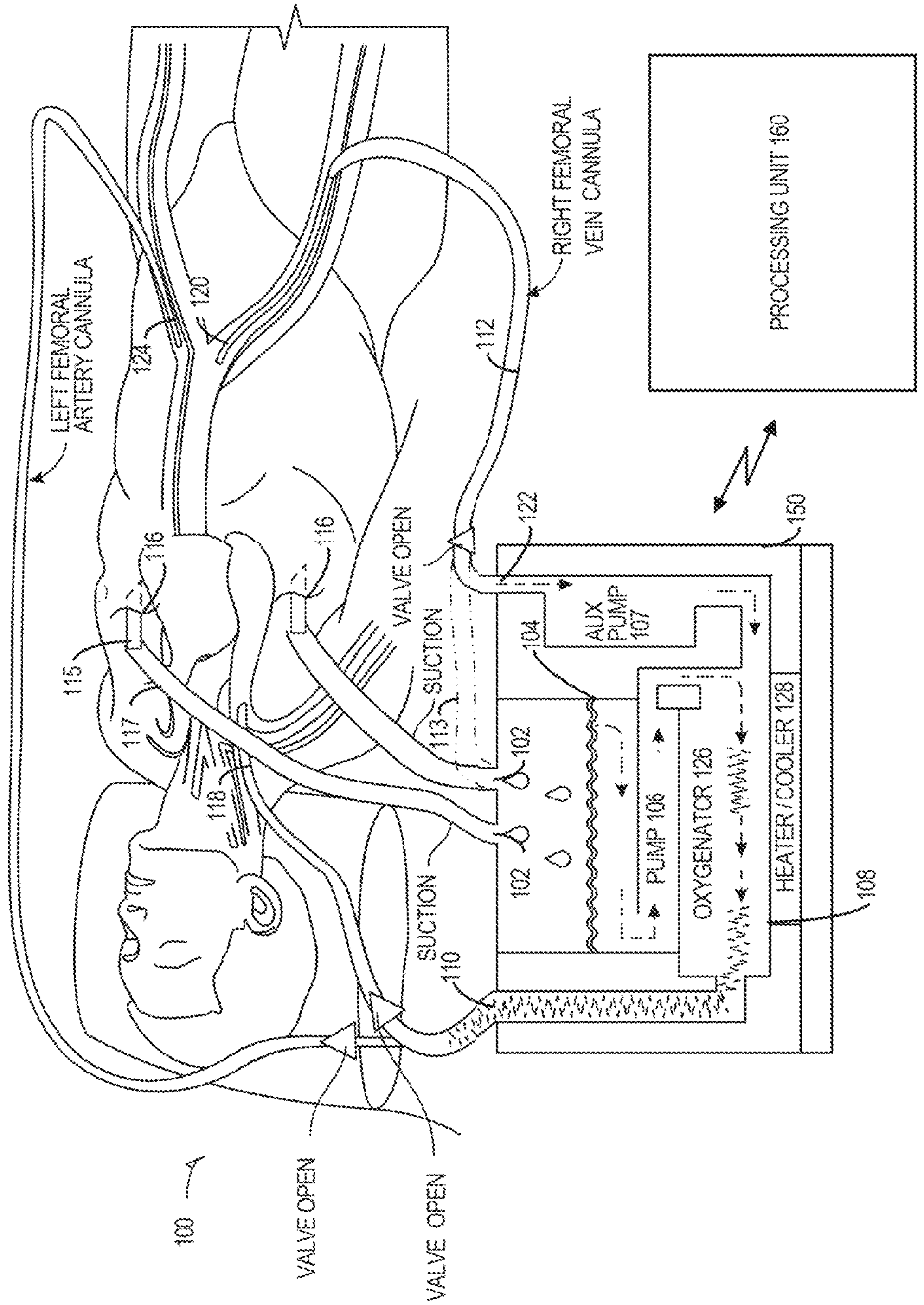
FIG. 1C depicts an example of a system for performing extracorporeal blood treatment of blood recovered from a subject.

FIG. 1A, FIG. 1B, and FIG. 1C each depict an example of a system for performing extracorporeal blood treatment of blood recovered from a subject. The system 100 can include a blood treatment device 150 including at least one first fluid inlet 102, a reservoir 104, a pump 106, a conditioner 108, and a first fluid outlet 110. The system can be configured to perform according to a plurality of different operating modes, and an individual mode can be selected based at least in part on a medical condition of the subject. For example, the system 100 can include a processing unit 160 included in, or otherwise communicatively coupled with, the blood treatment device 150. The processing unit 160 can include processing circuitry for monitoring at least one parameter of the blood recovered from the subject and to establish or adjust an operating parameter of the blood treatment device 150 based on the monitored blood. Ultimately, the plurality of different operating modes can be serially performed such as to progressively escalate treatment of the subject. Selection of an individual operating mode can at least in part be based on an indication of blood volume recovered, arterial blood gas (ABG), or an indication of blood lactate of the subject.

As depicted in FIG. 1A, the system 100 can perform according to an initial operating mode. The initial operating mode, also referred to herein as the "assist" mode, can be considered a standard or default operating mode of the system 100 and can be performed as a starting point for blood conditioning. For example, the initial operating mode can be initiated before receiving any indications of blood parameters. Blood can be received from a first blood transfer location 116 of the subject. Herein, "blood" can refer to mammalian whole blood, mammalian blood components such as red blood cells, platelets, and blood plasma, or another formulation of components which includes, at least in part, mammalian blood components. In an example, the first blood transfer location 116 can be a wound, an open surgical location, a bleeding site, or other type of fluid loss or hemorrhage location. In an example, the first blood transfer location 116 can correspond with an intrathoracic or intra-abdominal space of the subject, such as in the pleural cavity, the peritoneum, the retroperitoneal space, the thoracic or abdominal cavities. The first blood transfer location 116 can also correspond with a surgical location or an injury site in the extremities, such as a limb of the subject.

The system 100 can facilitate blood recovery from an intrathoracic area where the subject has sustained a wound or other pericardial or lung injury where access from exterior regions of the subject's body is undesired or unfeasible. For example, the system 100 can include or use a trocar 115 configured for tissue perforation and fluid or blood management. In an example, the trocar 115 can be sized and shaped to be inserted into the subject at the first blood transfer location 116. For example, the trocar 115 can include a diaphragm portion and a removable cannula. The diaphragm portion can be seated, via insertion of the cannula, at the first blood transfer location 116. The diaphragm portion can be expandable via inflation, vacuum, spring bias, or a similar mechanism to substantially secure and seal the diaphragm portion within the subject at the first location 116. In an example, the cannula can be removed following the seating of the diaphragm portion, and the diaphragm portion can establish a port into the intrathoracic or the intra-abdominal space of the subject. The system 100 can include or use a tube or conduit 117 sized and shaped to be inserted into the port for drawing blood from the subject and toward the blood treatment device 150.

The at least one first fluid inlet 102 of the blood treatment device 150 can be fluidly coupled to the tube or conduit 117. In an example, the system 100 can include or use a source of suction, e.g., a vacuum pump, to facilitate drawing of the blood from the first blood transfer location 116 and toward the reservoir 104. Alternatively or additionally, blood can be drawn from the first blood transfer location 116 passively, e.g., via gravity. For example, the blood treatment device 150 can be positioned such that the first blood transfer location 116 is at or near about or above a level of the reservoir 104, and such that gravitational forces can assist in directing the blood at least toward the first fluid inlet 102. As depicted, the first blood transfer location 116 can be accessed by a plurality of lines, such as via a plurality of trocars 115 or cannulas, for receiving blood into the reservoir 104. Multiple lines for drawing blood from the first blood transfer location 116 can be helpful, e.g., when an internal bleed spans a relatively wide area.

The reservoir 104 can collect the drawn blood, and an inline pump 106 fluidly coupled with the reservoir can move the blood toward the conditioner 108. In an example, the conditioner 108 can facilitate removal of carbon dioxide (CO2) from the blood before redistribution of the conditioned blood out of the first fluid outlet 110 and back to the subject. Alternatively or additionally, the conditioner 108 can regulate a temperature of the blood before similar redistribution. In the initial operating mode, the conditioned blood can be administered to the subject intravenously at a first return location 118 of the subject, e.g., into an internal jugular vein of the subject. Components of the blood treatment device 150, such as the reservoir 104, the inline pump 106, and the conditioner 108, are discussed in greater detail below with reference to each substantially similar component depicted in FIG. 2*a* and FIG. 2B.

In an example, the system 100 can include or use a reservoir bypass circuit 112. The reservoir bypass circuit 112 can be fluidly coupled to a primary fluid circuit of the blood treatment device 150. The reservoir bypass circuit 112 can be arranged such as to provide recovered blood from the subject, via a second fluid inlet 122, drawn from the subject via an auxiliary pump 107 toward the conditioner 108 and without entering the reservoir 104. For example, the reservoir bypass circuit can include or use the auxiliary pump 107 located in the reservoir bypass circuit 112 to help move recovered blood from the second fluid inlet 122 toward the conditioner 108. Alternatively or additionally, the system 100 can use a single pump, the inline pump 106, both for the primary fluid circuit and the reservoir bypass circuit 112. As depicted in FIG. 1A, the initial operating mode can involve the reservoir bypass circuit 112 being disengaged, disconnected, or otherwise not used, such that the inline pump 106 moves the entirety of the blood recovered from the subject through the reservoir 104. As depicted in FIG. 1A, FIG. 1B, and FIG. 1C, various circuits and fluid lines can be selectively engaged or disengaged via one or more actuators arranged to control respective valves of the circuit. For example, as shown in FIG. 1A and FIG. 1B, the processing unit 160 can control the one or more actuators such as to selectively engage or disengage the reservoir bypass circuit 112 and to initiate a particular operating mode. Alternatively, the various circuits and fluid lines can be manually clamped or disconnected from the primary fluid circuit at one or more locations, e.g., by a user, to selectively engage or disengage rather than be controlled by valves and actuators. In the initial operating mode, the second fluid inlet 122 is not used for blood recovery, no auxiliary pump 107 (if included) is active, and the entirety of the conditioned blood is received from the subject at the first blood transfer location 116, passed through the reservoir and exclusively through the inline pump 106 before being conditioned and distributed back to the subject exclusively at the first return location 118. In an example, the system 100 can condition blood at a flow rate within a range of about 1 liter per minute (L/min) and about 5 L/min while in accordance with the initial operating mode.

The blood treatment device 150 can be communicatively coupled with the processing unit 160. For example, the processing unit 160 can be located onboard the blood treatment device 150, or instead can be communicatively linked such as via wired or wireless connection. The processing unit 160 can include or use software for implementing one or more algorithms to monitor blood received from the subject and to establish or adjust at least one operating parameter of the conditioner 108 based on the monitored blood. For example, the at least one operating parameter can include a flow rate of the pump 106, a temperature regulation parameter of the conditioner 108, an oxygenation parameter of the conditioner 108, or an alert for an operator to move from the initial operating mode of the system 100 toward a different operating mode. In an example, the processing unit can include or use a machine learning model to determine an optimal set of parameter settings for the blood treatment device 150, conditioner 108, or other components (e.g., a sensor, valve, or pump). The machine learning method can continuously take measurement of data from the components over time, or when the device is turned on or re-initialized, in order to continuously iteratively improve the estimate to an optimal set of parameter settings. For example, the optimal set of parameter settings can include one or more desired blood flow rate settings or one or more granularity levels for the blood volume lost, temperature, oxygenation, or pH levels of the blood from the subject. Also, the processing unit 160 can predictively model blood or therapy requirements of the subject. For example, the processing unit 160 can include or use stored data to extrapolate, interpolate, or otherwise estimate likely future diagnosis or blood requirement of the subject. Such an estimation can be iteratively revised with subsequently received data.

FIG. 1B depicts an optional, intermediate operating mode of the system 100. The intermediate operating mode, also referred to herein as the “acidosis mode”, is substantially similar to the initial operating mode described above with reference to FIG. 1A. In an example, during performing the initial operating mode, the processing unit 160 can determine that a lactate concentration of the subject is worsening beyond a threshold parameter, such as a lactate concentration measured or predicted within a range of about 3 millimoles per liter (mmol/L) and about 5 mmol/L. Such a worsening trend can indicate that a subject is moving toward (or is in) a dangerous situation such as approaching lactic acidosis or an oxygen demand for blood that the subject will be unable to meet under the present operating parameters. Therefore, the processing unit 160 can generate or output a signal to the pump 106 or conditioner 108 to shift toward the intermediate operating mode. Here, the intermediate operating mode can involve temporarily increasing or intensifying the amount of therapy delivered via the system 100 in response to the determination that the lactate concentration is worsening beyond the threshold parameter. For example, the processing unit 160 can output a signal to the pump 106 or conditioner 108 to adjust a flow rate, temperature, oxygenation, or sweep gas parameter such as to increase a therapeutic effect of the system 100 on the subject. For example, the intermediate operating mode can involve the system 100 adjusting one or more operating parameters such as to condition the blood at a flow rate within a range of about 0.5 liters per minute (L/min) and about 7 L/min.

In an example, to help counteract a worsening trend in lactate concentration of the subject, performing the intermediate operating mode can involve drawing intravenous blood from the subject, such as via an intravenous cannula inserted at a second blood transfer location 120. For example, blood can be received from a femoral vein of the subject, e.g., to increase a fluid throughput and conditioning capacity of the system 100. As depicted in FIG. 1B, the intravenous blood drawn from the second blood transfer location 120 can be received at the second fluid inlet 122 and can enter the blood treatment device 150 via the reservoir bypass circuit 112. Alternatively or additionally, the intermediate operating mode can involve drawing intravenous blood from the subject at the second blood transfer location 120 and receiving the drawn intravenous blood at the at least one first fluid inlet 102 (according to the alternative depiction via phantom lines at 113). Here, the intravenous blood drawn from the second blood transfer location 120 can pass through the inline 106 without a need for the auxiliary pump 107 and without entering the reservoir bypass circuit 112. Both a blood volume received from the first blood transfer location 116 and a blood volume received from the second blood transfer location 116 can be conditioned via the conditioner 108 and administered back to the subject via the cannula into an internal jugular vein.

FIG. 1C depicts a controlled preservation mode of the system 100. Generally, the controlled preservation mode can be initiated to temporarily slow biological function of the subject such as to help preserve organ tissue. In an example, a controlled preservation mode of the system 100 can condition the subject's blood such as to induce a state of deep hypothermic arrest. Without being bound by theory, inducing a state of deep hypothermic arrest in the subject, toward a state of suspended animation, can lower a cardiac demand and can slow an increase of intercranial pressure for a subject experiencing TBI (Traumatic Brain Injury) and lactic acidosis.

In an example, during the performing of at least one of the initial operating mode or the intermediate mode, the processing unit 160 can determine, based on an indication that at least one of lactate concentration or ABG levels are worsening beyond a threshold parameter such that the subject is at or near a state of uncompensated shock or lactic acidosis. The transitioning to the controlled preservation mode can be based at least in part on a determination of a blood volume loss at a value between about 500 mL and about 1600 mL or at a value between about 750 mL and about 1500 mL. In an example, the transitioning to the controlled preservation mode can be based at least in part on a determination of a lactate concentration at or approaching a threshold value between about 1 millimole per deciliter (mmol/dL) and about 3 mmol/dL, such as a lactate concentration at or approaching less than about 2 mmol/dL. The transitioning to the controlled preservation mode can be based at least in part on a determination of ABG PH level at or less than around 7.2. Similarly, the transitioning to the controlled preservation mode can be based on a determination of blood pH at or approaching a threshold value between about 7.2 and 7.35, such as between about 7.25 and 7.3. The transitioning to the controlled preservation mode can be based at least in part on a determination of the subject's partial pressure of arterial oxygen (PaO2) at or approaching a threshold value less than about 60 millimeters of mercury (mmHg). Further, the transitioning to the controlled preservation mode can be based at least in part on a determination of the subject's partial pressure of $CO_2$ ($PCO_2$) at or approaching a threshold value greater than about 45 mmHg.

Before implementation of the controlled preservation mode, the system 100 can administer an alert or a prompt for a user, such as a technician or medical professional, to initiate a transition toward the controlled preservation mode by preparing 1) the second blood transfer location 120 at a femoral vein of the subject (if not yet used for intravenous drawing of blood) and 2) a second return location 124 at a femoral artery of the subject for intra-arterial return of conditioned blood. For example, the alert or prompt can instruct the user to cannulate the second blood transfer location 120 and the second return location 124 before authorizing implementation of the controlled preservation mode. As depicted in FIG. 1C, the blood treatment device 150 can draw blood from the second blood transfer location 120 via the reservoir bypass circuit, through the second fluid inlet 122. Here, the drawn blood can be introduced to the conditioner 108 via the auxiliary pump 107. Alternatively or additionally, the blood treatment device 150 can receive blood from the second blood transfer location 120 through the at least one first fluid inlet 102, into the reservoir, and via the inline pump 106 (according to the alternative depiction via phantom lines at 113). Thus, here a single pump (the inline pump 106) can move blood from the first blood transfer location 116 and the second blood transfer location 120 into the reservoir and toward the conditioner during operation of the controlled preservation mode.

In an example, the processing unit 160 can receive confirmation that the second blood transfer location 120 and the second return location 124 have been prepared to initiate the controlled preservation mode. Upon initiation of the controlled preservation mode, the processing unit can adjust operating parameters such as to lower a temperature of the conditioned blood toward a target first temperature within a range of about 30° C. and about 40° C. (e.g., toward a target first temperature of about 33° C.) via a heater/cooler 128 included in the blood conditioner 108. Returning blood to the subject at or near the target first temperature can lower the subject's myocardial oxygen demand and provide the subject's body at least temporary relief in an attempt to pull the subject out of uncompensated shock or lactic acidosis. The processing unit 160 can continue to monitor ABG levels and blood lactate concentration, following initiation of the controlled preservation mode, such as to determine whether a subject's state is improving or deteriorating. If the subject's state continues to deteriorate, the processing unit 160 can further adjust operating parameters such as to lower a temperature of the conditioned blood toward a target second temperature with a range of about 10° C. and about 25° C. (e.g., toward a target second temperature of about 18° C.) via the heater/cooler 128 and such that the conditioned blood is supplied to the subject at a relatively low target flow rate within a range of about 1 L/min and about 3 L/min, or within a range of about 1.5 L/min and about 2 L/min. The processing unit 160 can also facilitate administration of one or more pharmaceutical agents, selected to extend a time the subject can be suspended via deep hypothermic arrest and to limit ischemia-reperfusion injury (IRI) or reoxygenation injury. For example, the processing unit 160 can facilitate the administration of at least one of lidocaine, magnesium, nicardipine, milrinone, mannitol, calcium, magnesium, a pH-stat, or an alpha-stat. During suspension of the subject in deep hypothermic arrest, the processing unit 160 can continue to monitor a subject's condition. For example, the processing unit 160 can monitor at least one of body temperature, activated clotting time (ACT), ABG levels, or blood lactate concentration.

Operating the system 100 in the controlled preservation mode can afford a surgeon or other medical professional time to perform damage control physiological resuscitation (DCPR). For example, surgery can be performed during maintenance of temporary circulatory arrest via the processing unit 160 and via control of the conditioned blood supplied to the subject at the target second temperature and at the target flow rate. Once adequate surgical control of bleeding is achieved, a user can employ the blood treatment device 150 to slowly bring the subject back out of the induced state of deep hypothermic arrest and return the subject toward normal body temperature and blood flow rate. For example, the processing unit 160 can facilitate rewarming of the blood returned to the subject at the first return location 118 and the second return location 124. For example, the processing unit can monitor at least one of a temperature of the blood being intravenously returned to the first return location 118 or the temperature of the conditioned blood exiting an oxygenator 126 of the blood conditioner. In an example, the processing unit can calculate a target blood rewarming speed, such as to minimize air embolization. For example, the target blood rewarming speed can be within a range of about 0.1 degrees Celsius per minute (° C./min) and about 0.7° C./min, such as within a range of about 0.25° C./min and about 0.5° C./min.

Figure 2A:
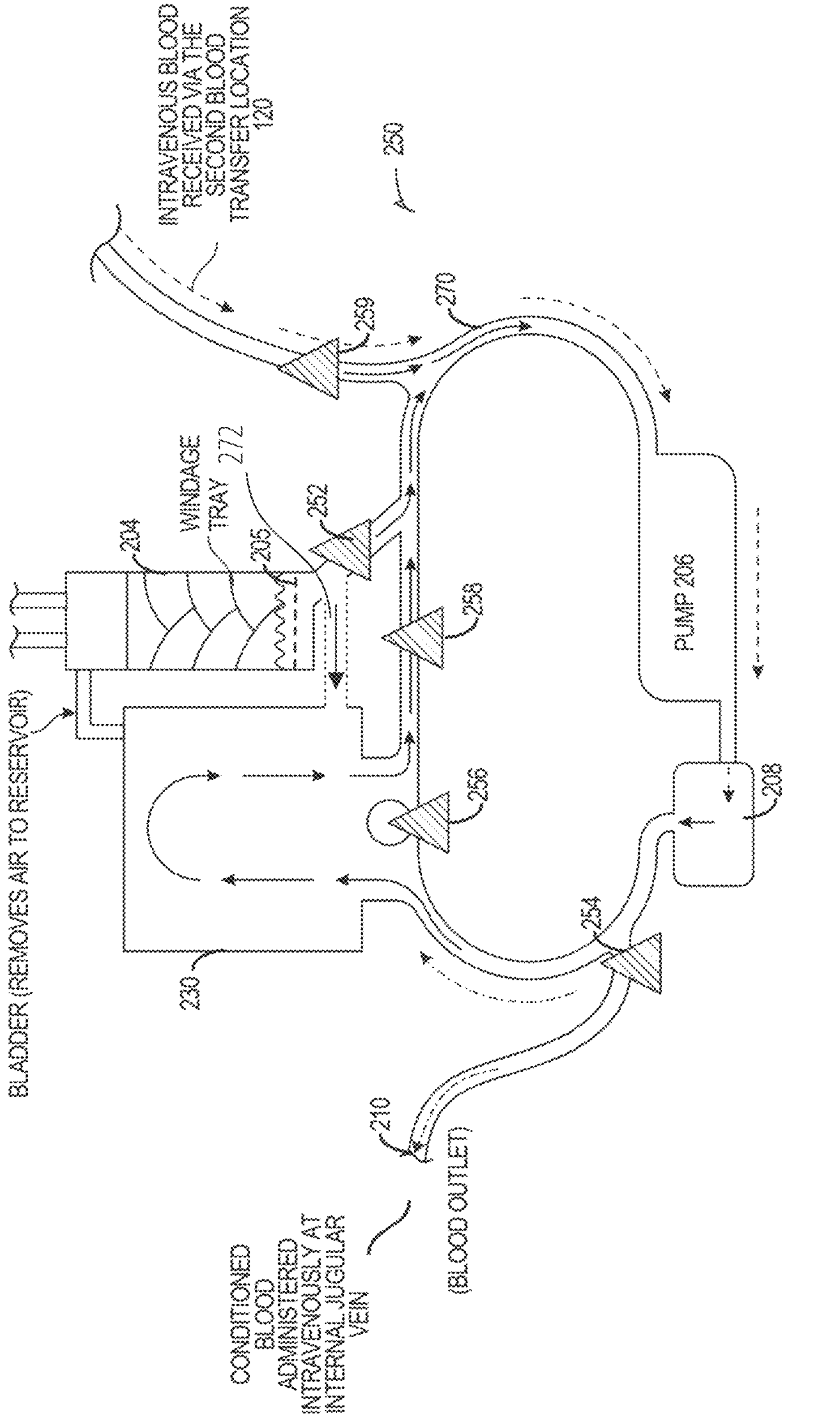
FIG. 2A depicts an example of a blood treatment device.
Figure 2B:
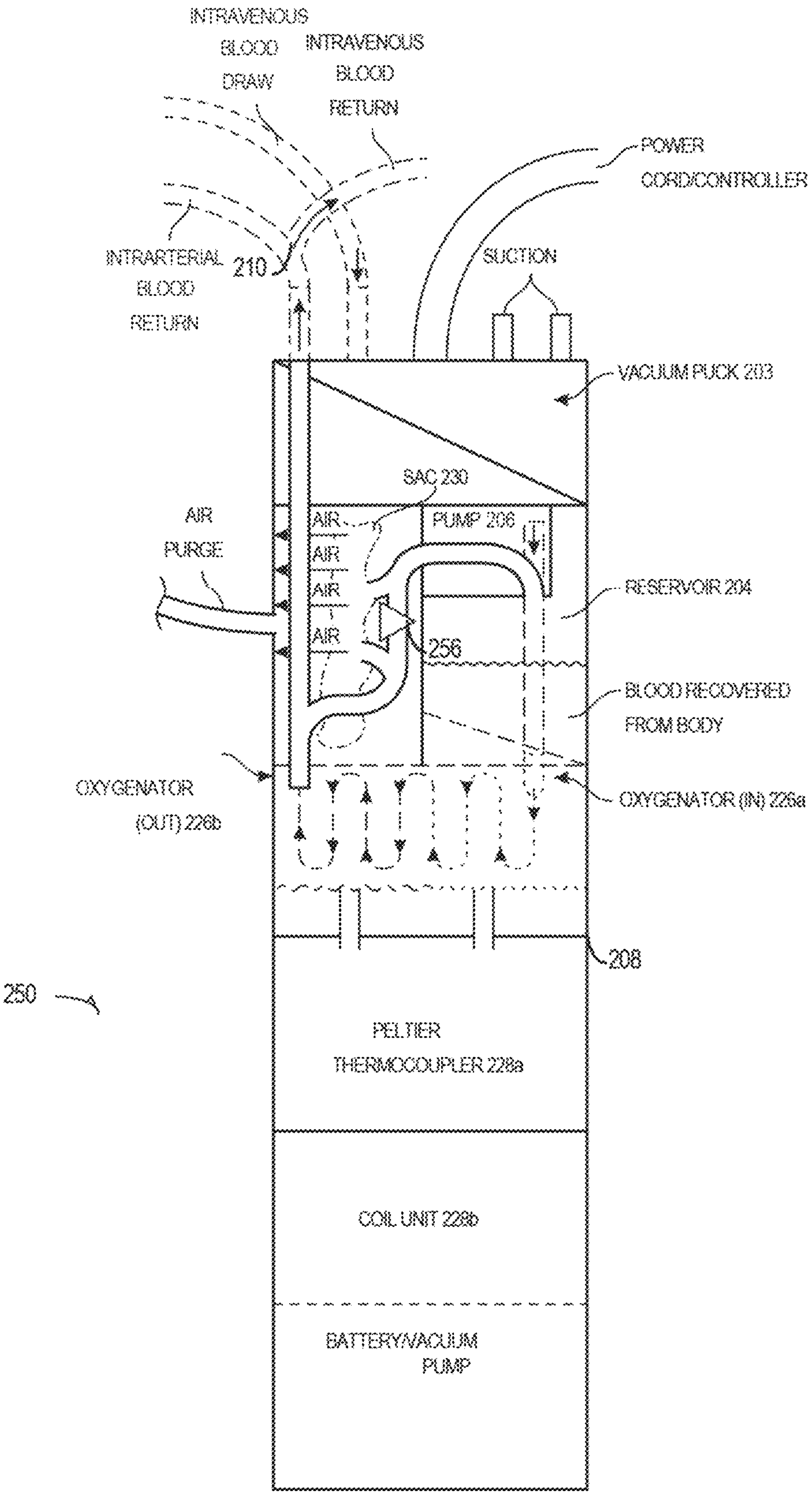
FIG. 2B depicts an example of a blood treatment device arranged within an enclosure.
Figure 2C:
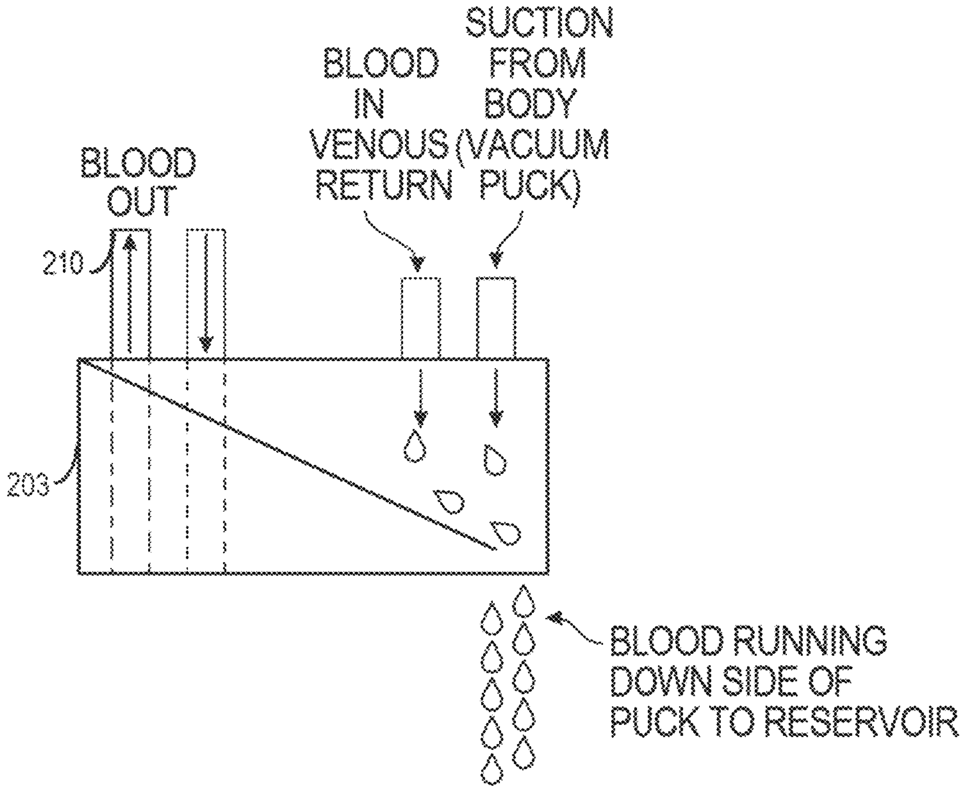
FIG. 2C depicts an example of a vacuum puck of a blood treatment device.

FIG. 2A and FIG. 2B each depict an example of a blood treatment device 250. The blood treatment device 250 is substantially similar to the blood treatment device 150 of FIG. 1A, FIG. 1B, and FIG. 1C. The components, structures, configurations, functions, etc. of the blood treatment device 250 can therefore be the same as or substantially similar to that described in detail above with reference to the blood treatment device 150. In an example and as depicted in FIG. 2A, the intravenous blood received via the second blood transfer location 120 (e.g., the femoral vein of the subject) can be incorporated into the primary fluid circuit 270 upstream of the pump 206. The blood treatment device 250 can further include an enclosed flexible bag, bladder, vesica, or sac 230 fluidly coupled with the blood conditioner 208 and arranged to receive conditioned, recovered blood therefrom. The enclosed flexible bag 230 can facilitate air purging from the primary fluid circuit 270 concurrent with blood treatment via the conditioner 208 and without stopping fluid flow or employing an air lock. For example, the enclosed flexible bag 230 can include a permeable or semipermeable membrane configured to contain fluid such as blood products while allowing diffusion of air and other gases through the membrane. In an example, the semipermeable membrane can include at least one of a microporous, nanoporous, chemical semi resistant, chemical resistant, anti-fouling polymer based material or other material or combination of materials having desired gas exchange or diffusion qualities while not permitting blood to permeate from the bag 230. The gas diffused from the bag 230 can be transported to an air evacuation port of the bag 230 and into the gas headspace of the reservoir 204. In another example, the gas diffused from the bag 230 can be released to the ambient environment. The enclosed flexible bag 230 can also be fluidly coupled to the reservoir 204, such as establishing an open loop hydraulic circuit with the recovered blood. Herein, an "open loop" circuit refers to configurations in which fluid is recirculated and selectively supplied to different locations while not fully recirculating the fluid to its original source. For example, the bag 230 can be fluidly coupled directly to an outlet of the reservoir 204 and fluidly coupled directly to an outlet of the conditioner 208. Also, herein the term "fluidly coupled" permits intervening, openable two-way valves such as valves 252, 254, 256, 258, and 259 depicted in FIG. 2. In an example, the primary fluid circuit 280 can include a valve 254 disposed between the bag 230 and conditioner 208, and the valve 254 can be operable to divert recovered blood exiting the bag 230 toward a blood outlet for redistribution back to the subject (e.g., via the internal jugular vein of the subject). For example, the valve 254 can be a diverter valve, a Y-valve, or a single two-way valve disposed on one end of a three-way or Y-shaped junction disposed between the bag 230 and the conditioner 208. The fluid circuit 270 can include a reservoir valve 252 and a cannulated blood line valve 259 which can be respectively engaged to allow a first portion of recovered blood from the reservoir and a second portion of recovered blood from the second blood transfer location 120 to be introduced into the primary circuit 270. In an example, the bag 230 can include a plurality of fluid connections with the primary circuit 270 and at least one bridge valve 256 disposed between the plurality of fluid connections. The bridge valve 256 can be opened to help equalize any pressure buildup within the bag 230 across the fluid circuit 270. For example, the bridge valve 256 can be temporarily opened when the reservoir valve 252 is closed to relieve excess volume accumulated in the bag 230. Thus, the reservoir valve 252 can facilitate protection of the red blood cells and Hb of the blood volume in the bag 230, such as preventing or limiting collapsed Hb from excess pressure. The fluid circuit 270 can also include a drainage valve 258. The drainage valve 258 can generally remain in an open position during operation of the device 250. However, when the reservoir valve 252 is opened and blood is being received by the fluid circuit 270 from the reservoir 204, the drainage valve 258 can be closed to help ease drainage from the reservoir 204. Also, when the drainage valve 258 is open, recovered blood from the bag 230 can reenter the circuit directly downstream of the reservoir 204 and be again circulated via the pump 206. Each of the valves 252, 254, 256, 258, and 259 can be independently engaged with respect to one another and can each be operated via a mechanical actuator, an electro-mechanical actuator, a pneumatic actuator, a solenoid actuator, a motorized actuator, a hydraulic actuator, a magnetic actuator, a computer actuator or microcontroller, a bimetallic strip, or a combination thereof.

In an example, the enclosed flexible bag 230 can be arranged in an at least partially open-to-air blood conditioning circuit (e.g., the circuit of the blood treatment device 250, an ECMO circuit, etc.) and be operated to mitigate air entrainment that develops from cycling blood through such a circuit. In certain other blood treatment systems it can be challenging to prevent unwanted air from entering the fluid system (e.g., air entrainment, cannula dislodgement or circuit disruption). For example, in certain other ECMO devices and circuits, it may become necessary to stop circulation and dispose of recovered blood upon detection of air entrainment exceeding a desired or tolerable level. The present inventor has recognized that the inclusion of the enclosed flexible bag 230 within the circuit can mitigate such undesired air entrainment, such as via temporarily pausing or stopping blood circulation in the conditioning circuit and "de-airing" the fluid circuit via the enclosed flexible bag 230 before resuming blood circulation and extracorporeal blood treatment. In an example, such a technique can facilitate air purging from the fluid circuit without having to dispose of blood that had previously accumulated greater than a desired or tolerable amount of air.

In an example, the enclosed flexible bag can include or includes a dedicated air purging line, e.g., connected to a source of pressure (e.g., a vacuum), such as connected via a one-way valve. The one-way valve can remain typically remain closed during circulation of blood through the fluid circuit and can be configured to open only upon in response to a detection of air by a microbubble sensor integrated within the one-way valve. Here, the one-way valve can divert entrained air safely away from the circulation pathway and preserving circuit integrity without exposing blood to ambient air. Alternatively or additionally, the one-way valve can be user-operable (e.g., manually opened and closed) such as to allow for user-initiated air purging. In an example, either of the reservoir valve 252 or the drainage valve 258 can be replaced with (or coupled inline with) an additional roller pump, such as to assist in drawing blood from the first blood transfer location 116 of the subject. In an example, such as where valve 252 is closed or not present in the primary circuit 270, the blood can be received from the first blood transfer location 116 of the subject, into the reservoir 204, and directly to the enclosed flexible bag 230 via the connection 272. In an example, the blood treatment device 250 can include one or more sensors (e.g., an analyte sensor, a flow volume sensor, a flow velocity sensor, a temperature sensor, or a combination thereof, such as embedded within or near the reservoir 204, the enclosed flexible bag 230, the pump 206, or any of valves 252, 254, 256, 258, or 259) to provide monitoring data of the blood during cycling through the blood treatment device 250. For example, the device 250 can include at least one sensor located upstream the conditioner 208 (e.g., embedded within or near the enclosed flexible bag 230, such as including the connection 272 being implemented). Also, the device 250 can include at least one sensor (e.g., an analyte sensor, a flow volume sensor, a flow velocity sensor, a temperature sensor, or a combination thereof) located downstream the oxygenator (e.g., embedded at or near an output of the oxygenator 208) to measure at least one of ABG, lactate, or temperature and to provide an indication of a blood quality that will be delivered from the device 250 back to the subject after conditioning. In an example, the enclosed flexible bag 230 can also include or be arranged adjacent to a heating element or radiator for adjusting a temperature of the blood within the enclosed flexible bag 230. In an example, the enclosed flexible bag 230 can include a sensor for closed loop control of heating using a sensed temperature and the heating element.

FIG. 2B depicts the blood treatment device 250 arranged within an enclosure. Such a compact arrangement can facilitate blood treatment methods described herein in non-hospital settings or in resource-poor environments. In an example, the blood treatment device can include or use a vacuum puck 203 arranged adjacent to the reservoir 204 and connected to a fluid headspace of the reservoir 204. As shown in the detail view in FIG. 2C, blood entering the vacuum puck 203 via the first blood transfer location 116 or the second blood transfer location 120 (depicted in FIG. 1B) can run down a side of the vacuum puck 203 toward the reservoir. In an example, the vacuum puck 203 can include a ramp or tilt such as to force blood down the side of the reservoir. In an example, a source of suction, such as an onboard vacuum unit, can facilitate suction of the blood into the reservoir 204 at a flow rate within a range of about 1 L/min and about 10 L/min, or within a range of about 2 L/min and about 6 L/m, e.g., at or near a flow rate of about 4 L/min. In an example, the source of suction can be disabled or impeded during an emptying of the reservoir 204 into the fluid circuit 270, such as when the valve 252 is opened (as depicted in FIG. 2A). In an example, the valve 252 can include an actuator or an additional intermittent pump that pulls blood from the reservoir.

The reservoir 204 can include or use a first filter for separating out larger particulates or unwanted materials, e.g., dirt, or metallic fragments from the blood or other fluid being transported into the reservoir. The first filter can also be arranged to prevent clots or larger proteins, such as fibrin, from progressing further along a fluid circuit of the primary circuit 270. The reservoir can also include a second filter for filtering ambient air that is drawn into the reservoir, such as to help maintain a sterile environment. The reservoir can also include or use windage tray, bubble-trap, or air separation chamber arranged to block or divert gases (e.g., bubbles or foam) away from the reservoir and to prevent gases from progressing further along the primary circuit 270. For example, the windage tray can provide a physical barrier between gases and blood or other fluid, and the windage tray can have openings arranged to allow lower density gases or air to rise and be vented or removed to an external atmosphere or be collected and processed. In situations where the reservoir becomes canted or inverted during the drawing of the blood from the first blood transfer location 116 into the reservoir, the windage tray can establish or maintain a desired or predetermined surface level of the fluid, e.g., the blood or other body fluid being processed or treated. For example, the windage tray can facilitate that the drawn blood or other body fluid is held at or above a predetermined surface level (e.g., corresponding with the dotted boundary 205 as shown in FIG. 2A) in the reservoir 204. This can help prevent unwanted bubbles or gases from entering the suction source or suction line, thereby preventing unwanted pressure surges and sudden flow increases. In an example, the windage tray can include or use one or more physical separation elements, such as baffles, vanes, grates, or textured surfaces.

The reservoir 204 can be sterile and fluidly sealed relative to an external ambient environment. The reservoir 204 can maintain a negative internal pressure relative to the external ambient environment, and the negative internal pressure can be provided at least in part by the source of suction. In an example, the reservoir 204 can include a reservoir pressure relief valve for the source of suction, and the pressure relief valve can be selectively engageable in response to detection of a clogging or obstruction at the trocar or chest tube. The reservoir pressure relief valve can help prevent damage to the reservoir 204 or to the tissue at the first blood transfer location 116 (as depicted in FIG. 1A). The reservoir 204 can include one or more filtration or air separation elements arranged therein to limit air bubbles, contaminates, or other unwanted components from further traveling in the fluid circuit of the blood treatment device 250. In an example, the reservoir 204 can be filled with blood toward a maximal internal volume, the maximum internal volume being within a range of about 500 cubic centimeters (cc) and about 2000 cc. In an example, the reservoir 204 can include or contain an anticoagulant such as heparin, bivalirudin, argatroban, enoxaparin sodium, a tissue-type plasminogen activator (tPA) or another anticoagulant or antiplatelet. Here, the anticoagulant can prevent subsequent clotting or clot formation within the blood treatment device 250. The anticoagulant, for example, can be added to the reservoir 204 prior to the blood being conveyed into the reservoir, mixed with the blood, or otherwise distributed with the blood within the blood treatment device 250.

The pump 206 can be arranged inline and spaced apart from (e.g., located upstream) the conditioner 208. The pump 206 can include a centrifugal blood pump (CBP) such as a magnetically levitated (maglev) pump, an impeller pump, a vaneless pump, a bearingless pump, or a combination thereof. The pump 206 can be configured to facilitate continuous pumping and delivery of blood from the reservoir toward and through the oxygenator. Herein, "continuous flow" can refer to blood flow over a significant period (e.g., greater than about 5 seconds) wherein the blood flow curve is substantially free of discontinuities (e.g., less than about 10% fluctuation in flow rate). When the fluid circuit of the blood treatment device 250 is subject to greater than a threshold flow resistance (e.g., greater than 200 mmHg/L/hr) downstream of the pump 206 (e.g., caused by a kink or obstruction in a fluid line), a CBP can respond by decreasing its speed or decreasing the rate at which it propels the blood until the flow resistance decreases. As such, a CBP can be advantageous to certain other blood pumps, such as in reducing damage to the blood by avoiding g-forces or transmembrane pressure gradients caused by high accelerations or decelerations. A CBP can also be advantageous in a fluid circuit in that it can withstand kinks or obstructions to the fluid line without bursting a fluid line or otherwise breaking a fluid seal of the fluid circuit. Alternatively or additionally, the pump 206 can include a pulsatile pump such as a roller pump, a diaphragm pump, or a peristaltic pump configured to facilitate pulsatile flow of the blood. The pulsatile pump can be configured to emulate a physiologic pulsatile flow of blood, e.g., a flow having a pulse waveform in a range of physiological pulse waveforms. Where the pump includes a pulsatile pump such as a roller pump, the primary circuit 270 can include one or more pressure sensors and the roller pump can be controlled (e.g., via a processing unit) to slow or stop a pumping operation where the system detects greater than a threshold line pressure caused by a kink or and obstruction. Moreover, if desired, when the system detects a decrease in blood flow caused by kinking or obstruction of a downstream fluid line, the system can either operate the pulse pump to increase flow from a zero (or minimum pulse volume) or have the system transition to a continuous-flow mode of operation.

As depicted in FIG. 2B, the blood conditioner 208 can include an oxygenator 226, a temperature regulator 228, or both. For example, an oxygenator 226 of the blood conditioner can include a silicon oxygen membrane or polymethylpentene (PMP) membrane for removing carbon dioxide ($CO_2$) from the recovered blood. Once $CO_2$ is removed, the recovered blood can cleave to hemoglobin (Hb) supplied in the oxygenator at a sweep gas rate within a range of about 2 L/min to about 6 L/min or about 4 L/min, and at a fraction of inspired oxygen ($FiO_2$) between about 10% and about 50% or an $FiO_2$ between about 21% and about 100%. In an example, the recovered blood passed through the oxygenator 226 of the blood conditioner can be hyper oxygenated, such as having a $PaO_2$ greater than about 100 millimeters of mercury (mmHg) or greater than about 200 mmHg. In an example, the blood conditioner 208 can use ambient air, such as ambient air exhausted from a vacuum pump or other source of suction, to help oxygenate the recovered blood. For example, the blood conditioner 208 can regulate a flow of ambient air between about 6 L/min and about 10 L/min, or at about 8 L/min. Also, supplemental $O_2$ can be supplied, e.g., via an external or onboard tank, in addition to the ambient air. For example, the supplemental $O_2$ can be supplied to help increase a net flow of air or sweep gas rate. Here, the supplemental $O_2$ can be supplied at a rate within a range of about 1 L/min and about 2 L/min. As such, the blood conditioner 208 can provide a net sweep gas rate between about 0.1 L/min and about 10 L/min, such as between about 7 L/min and about 9 L/min, while relying on supplemental $O_2$, provided via the external or onboard tank, being supplied a flow rate of less than 2 L/min.

The blood conditioner 208 can also include one or more heater/cooler units, such as a Peltier thermocouple **228*a* and a coil unit 228*b*. In an example, the Peltier thermocouple 228 can facilitate preheating of the recovered blood before it enters the oxygenator 226, such as to improve the oxygenation of the blood. This is because increased temperature has an inverse relationship to reaction time (e.g., removal of $CO_2$ and cleaving to hemoglobin (Hb)) and increases the rate of reaction, such that as the temperature increases, the number of molecules existing at higher energy levels increases. Also, the recovery blood may need to be cooled, involving the Peltier thermocouple 228*a* and a coil unit 228*b* to heat exchange the recovered blood from room temperature to a desired temperature range. For example, with reference to the controlled preservation mode of FIG. 1C, the coil unit 228*b* can be used by the blood treatment device 250 to induce a state of deep hypothermic arrest or ventricular fibrillation in the subject. This can range from, for example, a targeted temperature within a range of about 10° C. and about 30° C. The Peltier thermocouple 228*a* and the coil unit 228*b* can work in conjunction with each other or alone. In an example, the temperature regulator 228 can be physically separate from the oxygenator 226**, with the recovered blood passed back and forth, or the temperature regulator and oxygenator can be physically integrated.

Figure 3:
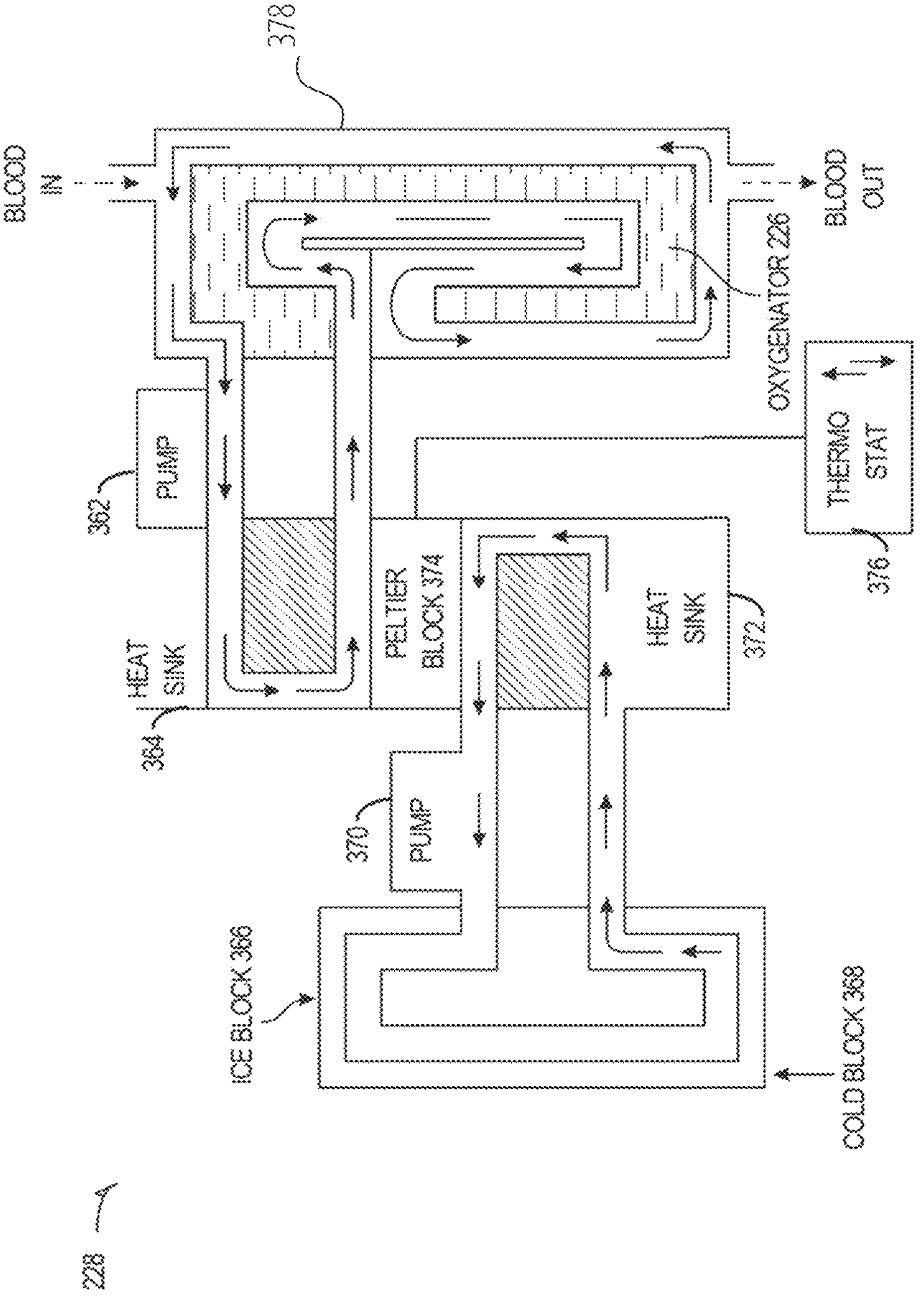
FIG. 3 depicts an example of an integration of the temperature regulator with the oxygenator in an example of a blood conditioner.

FIG. 3 shows an example of an integration of the temperature regulator 228 with the oxygenator 226 in a blood conditioner 208. For example, the blood conditioner 208 can include or use the oxygenator 226, an oxygenator pump 362, an oxygenator heat sink 364, an ice block 366, a cold block 368, a temperature regulator pump 370, a temperature regulator heat sink 372, a Peltier block 374 disposed between an oxygenator circuit and a temperature regulator circuit, and a thermostat 376. The oxygenator pump 362 can draw the recovered blood, e.g., from the reservoir 204 (as depicted in FIG. 2B). As the recovered blood passes through the oxygenator 226, $CO_2$ gas can be extracted from the recovered blood by diffusion across the oxygenator membrane. The rate of removal of $CO_2$ can be enhanced by concentrating a $CO_2$ sweep gas close to the surface of the membrane.

The Peltier block 374 can provide both heating and cooling output through separate interfaces via manipulation of electrical potential difference. Further, the Peltier block 374 can be compact, reliable, and efficient in thermoelectric cooling and heating applications involving heat exchange. Thus, the Peltier block 374 can be integrated in the blood conditioner 208 to operate in both cooling and heating modes, thereby providing an integrated cooling warming platform that can be used in a blood treatment device. In an example, the Peltier block 374 can function as a stand-alone heating element or cooling element utilizing temperature gradient with power provided to the Peltier block 374. Activation can be bi-directional to both heat and cool the functional blocks with switching capability. This can be accomplished via an electrical power controller system, which can direct the electrical current to the Peltier block 374 resulting in a change of direction of heat transfer and thus exchange. Such an arrangement can yield an efficient, rapid time response for blood heating and cooling operations to the desired temperature (e.g., within a range of about 10° C. and about 30° C.).

In an example, the temperature regulator 228 can include a heating element circuit 378. While the example in FIG. 3 shows the temperature regulator 228 as integrated with the oxygenator 226 (e.g., where the oxygenator 226 is embedded within a heating element circuit 378), the temperature regulator 228 can be similarly be integrated with one or more other components of the blood treatment device 250. For example, the heating element circuit 378 can include a tubing (e.g., formed of vinyl, polyethylene, silicone, polyvinyl chloride, etc.) that can at least partially enwrap or enclose a plurality of the components in the primary circuit 270 of the device 250 (each depicted in FIG. 2A), such as the reservoir 204, the pump 206, the blood conditioner 208, or the enclosed flexible bag 230. The heating element circuit 278 of the temperature regulator 228 can also at least partially enwrap or enclose an air blender 604, such as described with respect to FIG. 6 and FIG. 6B, and can also at least partially surround conduit connecting any of components such as the reservoir 204, the pump 206, the conditioner 208, the flexible bag 230, or the air blender 604.

In an example, the temperature regulator 228 can provide heat exchange over a surface area interface with blood in the primary circuit 270 of the blood treatment device 250 between about 2 meters squared ($m^2$) and about 15 $m^2$. In an example, the temperature regulator 228 can provide such heat exchange over a surface area between about 5 $m^2$ and about 12 $m^2$, such as greater than about 8 $m^2$. In an example, the temperature regulator 228 can provide such heat exchange over a surface area between about 2.5 $m^2$ and about 3 $m^2$, such as at about 2.78 $m^2$. For example, the surface area interface can include a heating element embedded within or wrapped around a tubing or conduit included in the primary circuit 270, e.g., to add heat at least before blood in the circuit 270 enters the blood conditioner 208.

In an example, the temperature regulator 228 can be controlled (e.g., via a processing unit 160 as depicted in FIG. 1A, FIG. 1B, and FIG. 1C) the based on an indication of patient blood temperature. For example, the temperature regulator 228 can be controlled based on monitored or received sensor data via first and second temperature probes of the blood treatment device 250. In an example, the first temperature probe can measure a first indication of blood temperature at or near a first blood transfer location 116, such as at or near the fluid inlet 102 or in the reservoir 104 (e.g., as depicted in FIG. 1A). The second temperature probe can measure a second indication of blood temperature at or near a first return location 118, such as at or near the first fluid outlet 110 or at an outlet of the conditioner 108 (e.g., as depicted in FIG. 1A). Monitoring of patient blood temperature entering and exiting the blood treatment device 250 can provide monitored temperature data to a control system to help enable the control system to accurately manipulate fluid flow rates and heat exchange mechanisms as improve regulation of patient body temperature. For example, the first and second temperature probes can be included in a thermostat of the temperature regulator 228, and data from the first and second temperature probes can be used to condition blood, e.g., received from a hemorrhage of a patient, toward a specified, desired temperature.

Figure 4A:
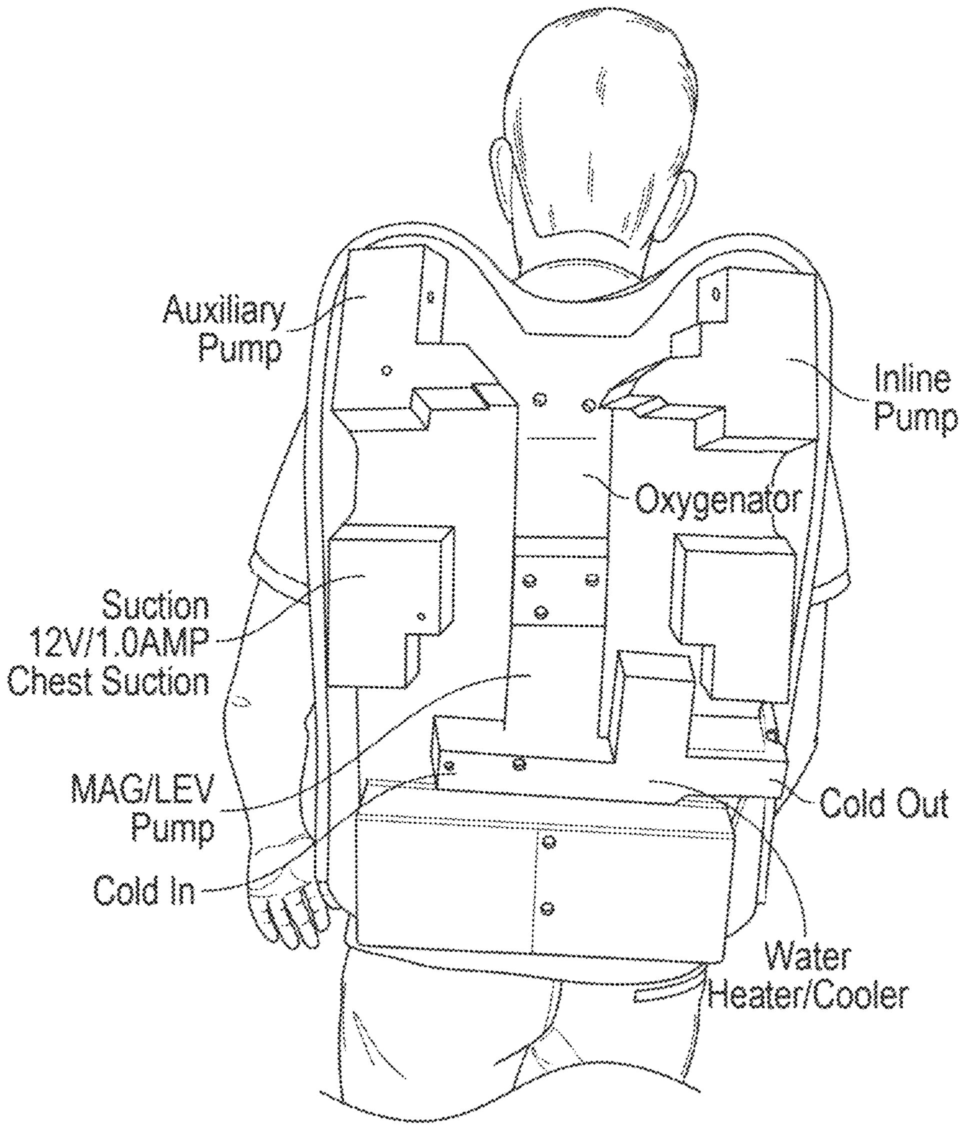
FIG. 4A depicts an example of a system for performing mobile, extracorporeal blood treatment of recovered blood.
Figure 4B:
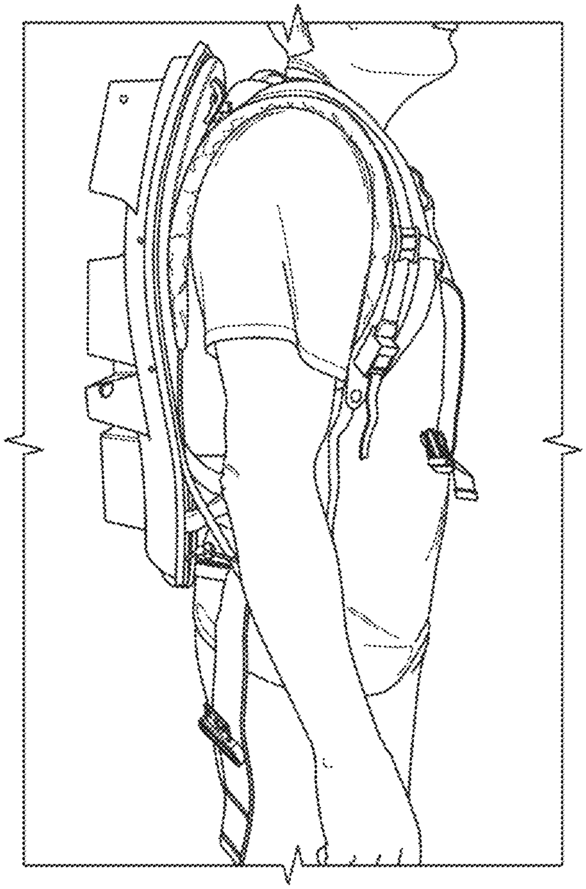
FIG. 4B depicts an example of a system for performing mobile, extracorporeal blood treatment of recovered blood.
Figure 4C:
FIG. 4C depicts an example of a system for performing mobile, extracorporeal blood treatment of recovered blood.

FIG. 4A, FIG. 4B, and FIG. 4C depict another example of a system for performing extracorporeal blood treatment of recovered blood. As shown in FIG. 4A, the system described with respect to FIG. 1A, FIG. 1B, and FIG. 1C as well as the devices described with respect to FIG. 2A, FIG. 2B, and FIG. 2C can be integrated into a mobile trauma management system. For example, such a mobile trauma management system can enable a medic or other technician to assist an injured person in the field, such as away from a hospital operating room setting. For example, the field may be a battlefield, a war zone, a remote area, an ambulance, or a conflict-affected area. In an example, the mobile trauma management system can include a system for blood treatment that is substantially similar to that described with respect to FIG. 1A, FIG. 1B, and FIG. 1C. As shown in FIG. 4A and FIG. 4B, the blood treatment device can be mounted on a carrier such as a backpack including straps. As shown in FIG. 4C the carrier can include a lightweight frame e.g., fabricated with carbon fiber, aluminum, heat-treated thermoplastic polymers, ABS (acrylonitrile butadiene styrene), polystyrene (PS), polycarbonate (PC), or polypropylene (PP). Such a carrier can weigh less than about 10 pounds (lbs) to promote ease of transport. The carrier can optionally also include an internal battery or battery pack operatively engaged with the blood treatment device. As depicted in FIG. 4A, a back panel of the carrier can define recesses sized and shaped to receive components such as an oxygenator, a source of suction, one or more pumps, and a temperature regulation unit. When the mobile trauma management system is removed from the back of the medic or technician, opened, and laid out, the carrier can form a sterile surface from which to perform the procedures described herein.

Figure 5A:
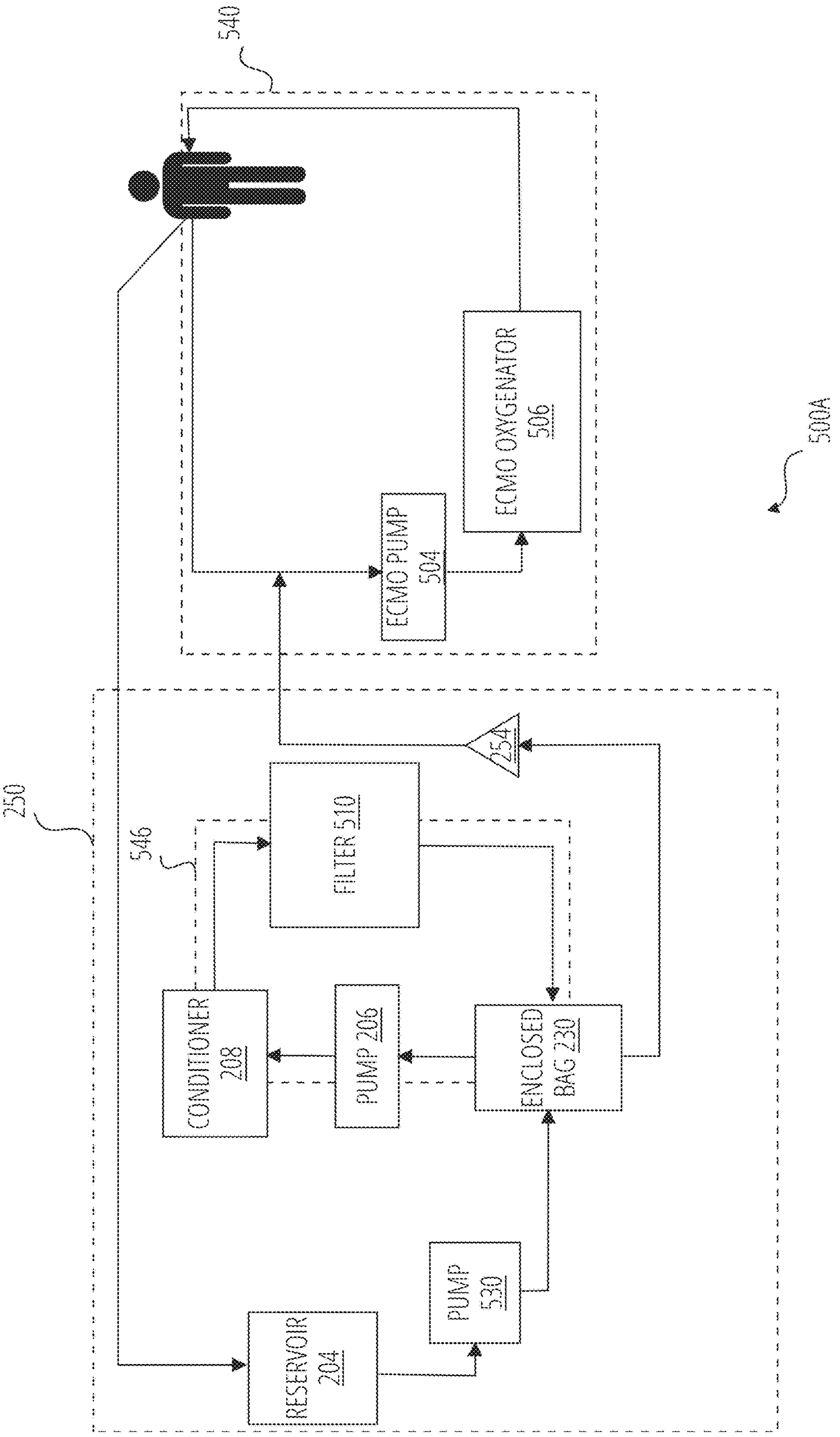
FIG. 5A depicts an example of a system for performing extracorporeal blood treatment of recovered blood.

FIG. 5A depicts an example of a system for performing extracorporeal blood treatment of recovered blood. The system 500A can include the blood treatment device 250, e.g., connected in parallel to an ECMO circuit 540 for concurrent, dual oxygenation of blood received from (e.g., at or near a hemorrhage of) a human subject. For example, the system 500A can include an ECMO pump 504, an ECMO oxygenator 506, a reservoir 204, an enclosed flexible bag 230, and a conditioner 208. The combination of the respective circuits of the device 250 and the ECMO circuit 504 can, in some instances, facilitate hyperoxygenation of blood received from and distributed back to the subject.

The ECMO circuit 540 includes the ECMO pump 504, which can be configured as a centrifugal pump, a magnetically levitated centrifugal pump (e.g., configured with magnets made of neodymium and/or other suitable materials), a roller pump, or a combination thereof. The ECMO pump 504 can include a port to receive (e.g., facilitate removal of) blood from the human subject (e.g., via a vein, internal bleed, or a hemorrhage of the subject) and a fluid conduit to introduce the removed blood to the ECMO oxygenator 506. The ECMO oxygenator 506 can include a gas-tight confinement (e.g., a secure housing or enclosure) where fresh gas is introduced to the ECMO oxygenator. For example, the fresh gas can be induced, e.g., via an air blender, to flow within the ECMO oxygenator 506 in a direction counter-current to blood introduced to the circuit and can flow over, through, or otherwise associated with a gas-permeable membrane or other diffusion structure of the oxygenator 506. For example, with the ECMO pump 504 rotating in a first or forward direction, blood can flow from a blood inlet of the ECMO oxygenator 506 toward a blood outlet of the ECMO oxygenator 506, while fresh gas can flow from a gas inlet (e.g., arranged opposite the blood inlet) in the ECMO circuit to a gas outlet of the ECMO oxygenator 506. Here, the blood can flow over the gas-permeable membrane (e.g., a gas-permeable hollow fiber, a gas-permeable capillary structure, a gas-permeable flat sheet, a diffuser present outside a membrane material, etc.) carrying oxygen from the gas to the blood, while by-products (e.g., carbon dioxide) of blood are transported from the blood to the gas. The blood can exit the oxygenator 506 at an outlet to be returned to the circulation of the subject, and the used gas can be discarded or scrubbed for remaining oxygen before being eventually discarded as exhaust.

As depicted in FIG. 5A, the blood treatment device 250 (as described with respect to FIG. 2A, FIG. 2B, and FIG. 2C) can be connected with the ECMO circuit 540 to establish the system 500A for performing extracorporeal blood treatment of recovered blood. For example, concurrent with the ECMO pump 504 moving blood from the human subject toward the ECMO oxygenator 506, a reservoir 204 can receive blood from the human subject (e.g., via a port into and a fluid conduit from a vein, internal bleed or a hemorrhage of the subject). The reservoir 204 and the ECMO pump 504 can each receive blood from the same patient location (e.g., each from the first blood transfer location 116 of FIG. 1A), or alternatively can each receive blood from a different patient location, such as one from a vein and the other from a hemorrhage of the subject.

In an example, the blood treatment device 250 can include a roller pump 530 connected in line with the reservoir 204 (such as directly upstream or directly downstream the reservoir). The roller pump 530 can facilitate removal (e.g., via suction) of blood from the human subject and collection thereof into the reservoir. In an example, blood can pass from the reservoir directly toward the enclosed flexible bag 230 (such as via the connection 272). The pump 206 can facilitate movement of blood in the enclosed flexible bag 230 toward the conditioner 208. In an example, the blood can be recirculated, such as through the enclosed flexible bag 230 and the conditioner 208, in a loop 546. In an example, the loop 546 can further include a filter 510 arranged inline between the conditioner 208 and a return port to the enclosed flexible bag 230. For example, the filter (e.g., a hemoconcentrator, a potassium-removing or other chemical constituent-removing filter, a mechanical screen, etc.) can selectively remove blood impurities, particulates, or other contaminants from the conditioned blood.

Following conditioning via the conditioner 208, (e.g., following at least one recirculation within the loop 546), the blood from the blood treatment device 250 can be selectively introduced to the ECMO circuit 540 via a valve 254. For example, an operator or a technician can determine when the conditioned blood from the blood treatment device 250 ought to be introduced to the ECMO circuit 540 based on sensor data or a flow rate within at least one of the primary circuit fluid circuit 270 (as depicted in FIG. 2A) or the ECMO circuit 540. The valve 254 can additionally or alternatively be operated based on a trigger or command from the processing unit 160 (as depicted in FIG. 1A), such as via an actuator controlled by a microcontroller. Introduction of the blood, conditioned via the blood treatment device 250, e.g., upstream the ECMO pump 504 for further oxygenation via the ECMO oxygenator can help facilitate an additive effect or synergistic effect in which oxygenation is enhanced, providing the subject with an improved or optimized amount of oxygen (e.g., as measurable via the saturation level of oxygen in their blood). For example, the additive effect, or the concurrent or parallel operation of the blood treatment device 250 and the ECMO circuit 540, can result in more oxygen being available for improving the physiological function or preservation of the subject.

Figure 5B:
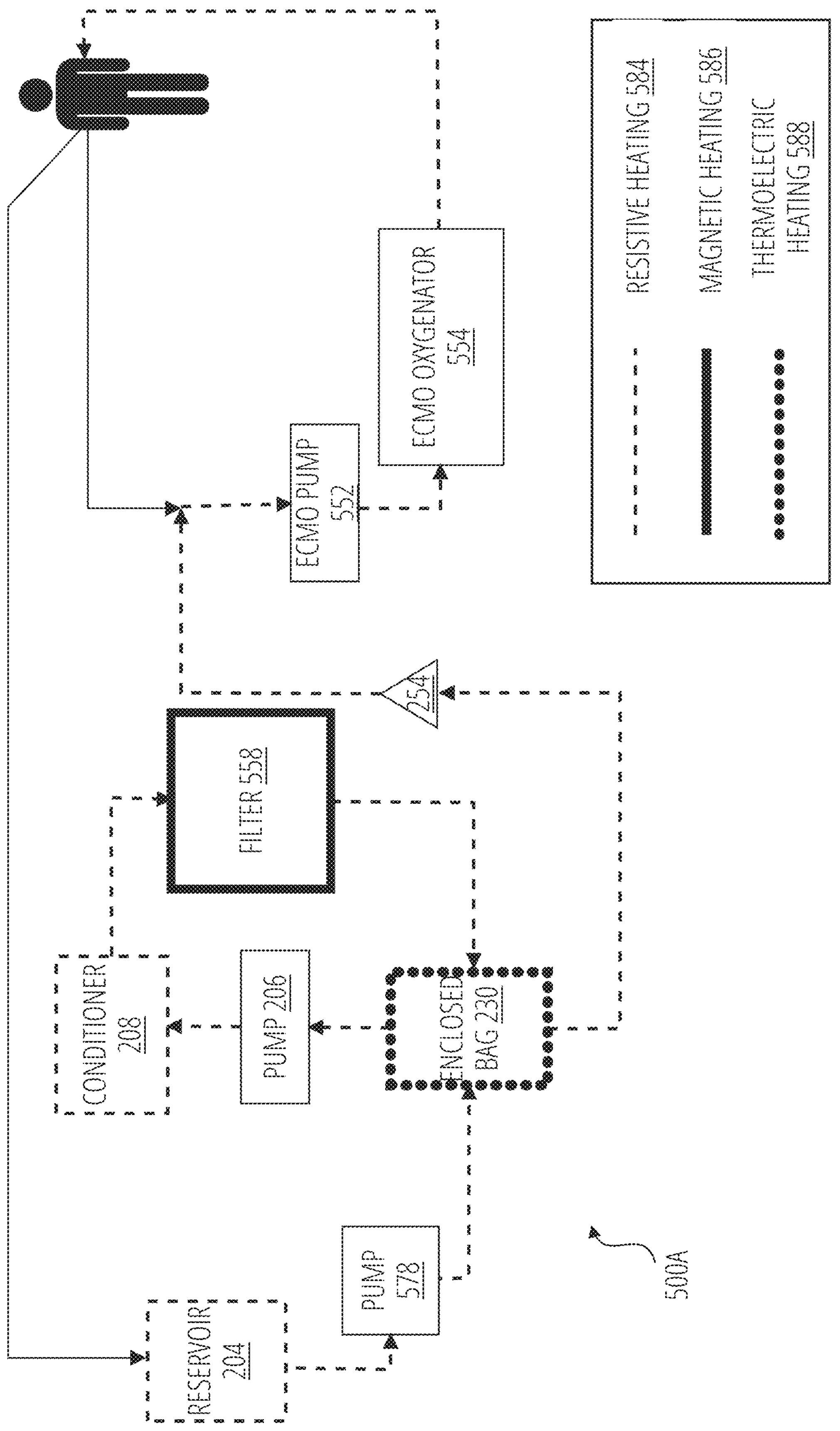
FIG. 5B depicts an example of a system for performing extracorporeal blood treatment of recovered blood, showing various blood heating modalities along the fluid circuit.

FIG. 5B depicts an example of a system for performing extracorporeal blood treatment of recovered blood, showing various blood heating modalities along the fluid circuit. Similar to that previously described with respect to FIG. 3, certain portions of the fluid circuit in the blood treatment device 250 (e.g., portions of the system 500A, as depicted in FIG. 5B) can include or use a heat exchanger configured to at least heat patient blood concurrently with conditioning and delivering the blood back to the patient. Despite the heating modalities described below and depicted with respect to system 500A of FIG. 5B include and describe the ECMO circuit 540 of FIG. 5A, they can similarly be applied to the blood treatment device 250 as shown and described with respect to FIG. 2A and FIG. 2B, e.g., where no ECMO circuit 540 is present in the blood conditioning circuit. In an example, the system 500A can include one or more heat exchangers, respectively arranged for at least one of resistive heating 584, magnetic heating 586, or thermoelectric heating 588. For example, portions of the fluid circuit depicted in FIG. 5B with the thin dotted line indicating the resistive heating 584, such as the reservoir 204, the pump 567, the enclosed bag 230, the conditioner 208, the valve 254, and various conduits therebetween (and notably, a final conduit through which the conditioned blood is ultimately delivered back to the patient) can each be enwrapped or otherwise contacted with coil or tubing for transferring electrical energy (e.g., current) into heat which ultimately warms the blood during the circulation of blood through the system 500A. Portions of the fluid circuit depicted in FIG. 5B with the bold solid line indicating magnetic heating 586 (e.g., the filter 558) can include or be contacted with a magnetic heat exchanger (e.g., an electromagnetic heat exchanger, a magnetic turbulator, an inducting heater, etc.) arranged to transfer heat, e.g., via thermomagnetic convection such as via ferrofluids. Portions of the fluid circuit depicted in FIG. 5B with the bold dotted line indicating the thermoelectric heating 588 (e.g., the enclosed bag 230) can include or be contacted with a thermoelectric heat exchanger (e.g., a Peltier heater/coolers such as the Peltier block 374 as depicted in FIG. 3), arranged to transfer heat, e.g., via electrical current or a temperature difference in thermoelectric materials. For example, the system 500A including a plurality discrete heat exchangers, each configured to provide one of the resistive heating 584, the magnetic heating 586, and the thermoelectric heating 588 can facilitate energy-efficient blood warming that provides dynamically controllable heating, e.g., based on a severity of hypothermia of the patient. Such dynamic control over heating can be especially important during extracorporeal blood treatment in hypovolemic or coagulopathic trauma patients.

In an example, the system 500A can include processing circuitry (e.g., the processing unit 160 of FIG. 1A or the processor 802 of FIG. 8) for controlling operation of the plurality of discrete heat exchangers (e.g., each of the resistive heating 584, the magnetic heating 586, and the thermoelectric heating 588 elements) such as to operate the heating of the blood concurrent with extracorporeal treatment and delivery of the blood back to the patient, in a plurality of different operating modes. For example, based on an indication of a normothermic patient state (e.g., indicative of mild or no present patient hypothermia, such as a patient having an average core temperature less than about 35° C.) the processing circuitry can activate the thermoelectric heating 588 element, such as via the heat exchanger integrated with the enclosed bag 230. Here, the resistive heating 584 and the thermoelectric heating 588 elements can remain inactive or operated at reduced power. Such operation can provide relatively low-power thermal regulation to promote battery efficiency, which can be helpful for prolonged casualty care e.g., in resource-limited or prehospital environments.

Based on an indication of a moderate hypothermia patient state (such as a patient having an average core temperature within a range of about 32° C. to about 35° C.), the processing circuitry can activate a) one or more the resistive heating 584 elements (e.g., one or more coils or tubes enwrapping portions of the fluid circuit) and concurrently, b) the thermoelectric heating 588 element. Here, the resistive heating 584 elements can be arranged in direct thermal contact with the blood in the fluid circuit during storage in the reservoir 204, conditioning, and throughout various points of travel through the circuit and back to the patient, providing rapid heat transfer while still maintaining a relatively conservative energy profile. Here, the resistive heating 584 elements and the thermoelectric heating 588 element can be independently operable to each other, such as to facilitate scalable response based on flow rates and target rewarming speed (e.g., scaling heating via changing a heating intensity via the resistive heating 584 while maintaining a relatively constant level of heating via the thermoelectric heating 588).

Based on an indication of a sever hypothermia patient state (such as a patient having an average core temperature greater than about 32° C.), the processing circuitry can activate a) one or more the resistive heating 584 elements (e.g., one or more coils or tubes enwrapping portions of the fluid circuit) b) the thermoelectric heating 588 element, and the magnetic heating 586 elements concurrently, such that all three heating modalities become activated. Such collective, concurrent heating via each of the resistive heating 584, magnetic heating 586, and thermoelectric heating 588 modalities can provide relatively aggressive, life-sustaining rewarming therapy during the extracorporeal conditioning (e.g., oxygenation) and delivery of the conditioned back to the patient. Here, the magnetic heating 586, while relatively power-intensive, can facilitates deep and rapid volumetric heat delivery to the blood via magnetic the exchanger core. Such a mode can prioritize heat delivery over energy conservation, such as to reflect an urgency of restoring normothermia in certain cases of profound thermal injury.

In an example and in addition to the blood warming via the any of the resistive heating 584, the magnetic heating 586, or the thermoelectric heating 588, the system 500A can include a first chemical heating apparatus. The chemical heating apparatus can include a plurality of chemicals selected such that, when combined, facilitate an exothermic reaction from a buffered solution. In an example, such a chemical heating apparatus can help warm blood that is passing through an interior of the conditioner 208 (e.g., at or near an inner plate of a blood oxygenator). Alternatively or additionally, the system 500A can include a second chemical heating apparatus, arranged to contact the surface area of certain components of the fluid circuit, such as the reservoir, the enclosed bag, the conditioner, conduits provided therebetween, or a combination thereof. Here, the second chemical heating apparatus can be operated in a similar fashion to that described above with respect to the first chemical heating apparatus, resulting in an exothermic reaction that provides heat to certain portions of the fluid circuit. In an example, the second chemical heating apparatus can be operated (e.g., reagents mixed to cause the chemical reaction) as a part of an initial device startup sequence, such as to prime or prewarm certain components of the circuit before subsequent heating via at least one of the resistive heating 584, magnetic heating 586, or thermoelectric heating 588 elements. During such an initial device startup sequence, the second chemical heating apparatus can be activated, and a priming fluid (e.g., saline, dextrose 5%, or other sterile fluid) can be circulated through the fluid circuit before blood is drawn from the patient, such as to help prewarm the circuit to subsequently receive and treat the blood. In an example, such an initial startup sequence can involve warming the priming fluid (and in turn, certain components of the fluid circuit through which the priming fluid is passing) from about 70° C. to about 104° C. Such a preheating or priming of the fluid circuit in the system 500A can help avoid a need to use battery power to initially bring the system 500A up to an appropriate operating temperature for processing human blood.

Figure 5C:
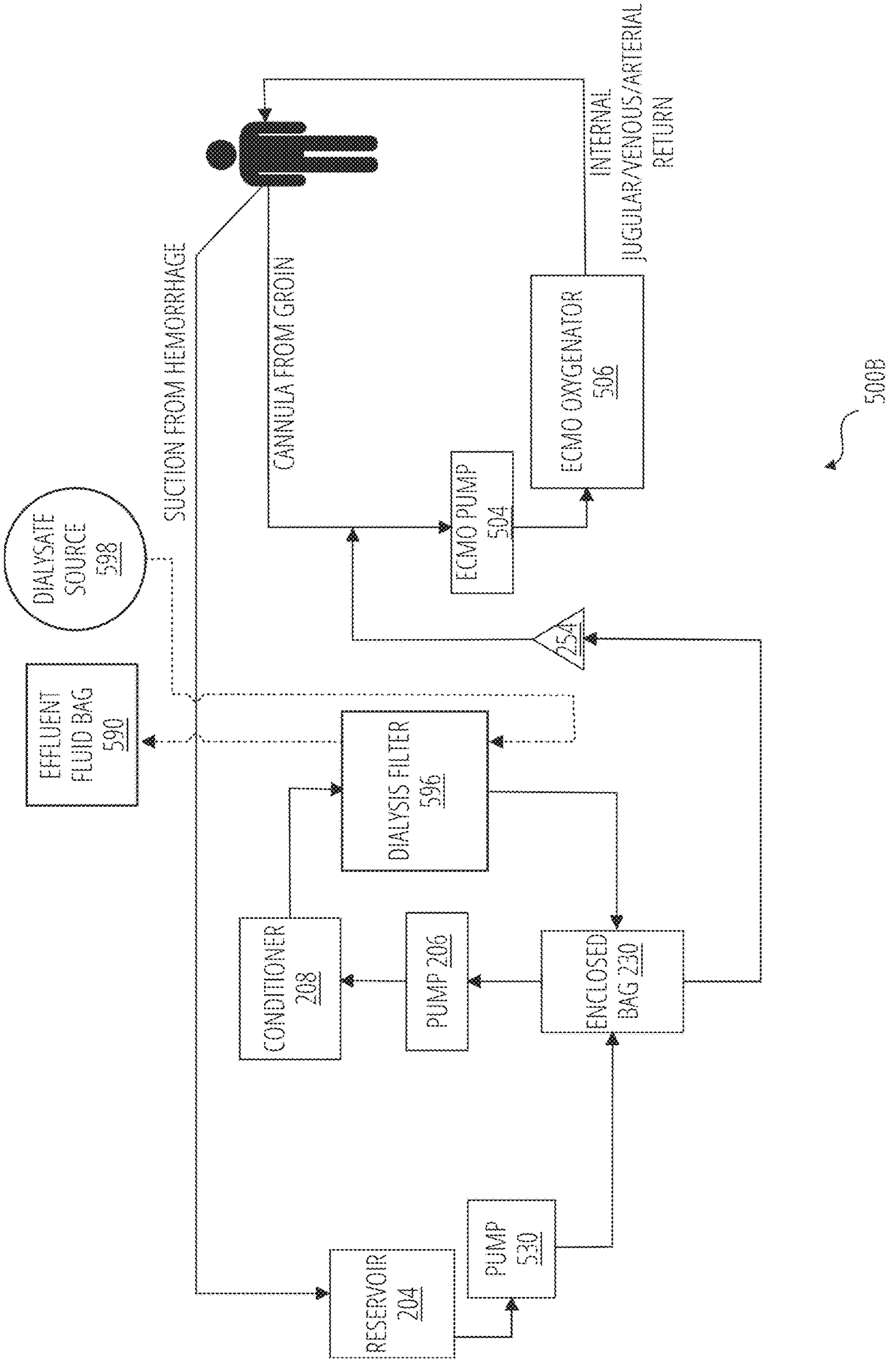
FIG. 5C depicts an example of a system for performing extracorporeal blood treatment of recovered blood, including batch-mode dialysis for trauma resuscitation.

FIG. 5C depicts an example of a system for performing extracorporeal blood treatment of recovered blood, including batch-mode dialysis for trauma resuscitation. Combat trauma, hemorrhagic shock, rhabdomyolysis, and battlefield-induced acute kidney injury (AKI) can be often accompanied by lethal acid-base and metabolic derangements. Elevated serum lactate (e.g., ≥4 mmol/L) can provide an indicator of shock severity and mortality, and rising lactate can reflect both tissue hypoperfusion and inflammatory-driven mitochondrial dysfunction. Certain other renal replacement therapies (RRT) can be unsuitable for the prehospital or field-deployed setting, such as being too slow or impractical. The present inventor has recognized the benefits of an extracorporeal blood conditioning system that provides significant lactate clearance as well as clearance of certain other toxic solutes in the early phase of trauma resuscitation, such as to avoid or mitigate damage to renal and cellular systems. In certain situations where the patient is exhibiting acute lactic acidemia (lactate level >5), it can be challenging to provide blood conditioning to sufficiently clear lactate through oxygenation alone. Implementation of rapid batch-mode dialysis alongside the extracorporeal blood treatment can help facilitate additional lactate clearance. For example, the system 500B can be similar in many respects to the system 500A described with respect to FIG. 5A and FIG. 5B. Here, the system 500B can include a dialysis filter 596, such as fluidly coupled to a dialysate source 598 and an effluent fluid bag 590 or other purge location. The system 500B can, at least partially via the dialysis filter 596, facilitate high-efficiency clearance of blood lactate, potassium, urea, myoglobin, and inflammatory cytokines, e.g., concurrent with blood conditioning via the conditioner 208 and over specified period of time (e.g., within about 15 minutes, about 20 minutes or about 30 minutes).

In an example, the system 500B can include processing circuitry (e.g., the processing unit 160 of FIG. 1A or the processor 802 of FIG. 8) for controlling a rate of dialysate intake, such as to facilitate relatively high-dose, intermittent hemodialysis of the blood in batches. For example, the processing circuitry can operate the system 500B such as to provide dialysis treatment to a specified volume of blood (e.g., at a volume within a range of about 0.6 liters (L) to about 3.0 L, such as about 1.5 L), to promote scalable and predictable solute removal. Unlike certain other approaches to dialysis which primarily targets uremia, the system 500B can include at dialysis filter 596, a dialysate source 598, and be controlled via the processing circuitry to instead primarily target early lactate reduction such as to reverse metabolic acidosis, blunt systemic inflammation, and restore certain mitochondrial function and immune regulation in the patient. For example, the dialysis filter 596 can include a diffusion-optimized high-flux membrane. Also for example, the processing circuitry can control batch dialysis with relatively high dialysate-to-blood flow ratios (e.g., ratio of dialysate flow rate to blood flow rate (Qd:Qb) greater than about 1:1). In an example, the system 500B can be arranged such that the dialysate flows from the dialysate source 598 in an opposite direction to the direction of blood flow, such as to provide counterflow between the blood and the dialysate across the dialysis filter 596.

In an example, the system 500B can facilitate greater than about 40% lactate reduction per blood circulation cycle, where starting lactate is greater than about 6 millimoles per liter (mmol/L). Table 1 below depicts certain operating parameters of the system 500B, such as controlled by the processing circuitry, to facilitate a desired dialysis during extracorporeal treatment of blood.

TABLE 1

| | |
|---|---|
| Blood Flow Rate (Qb) | 60-1500 mL/min via magnetically levitated pump |
| Dialysate Flow Rate (Qd) | 60-3000 mL/min (motorized, countercurrent) |
| Treated Blood Volume | 0.6-3.0 L per batch |
| Treatment Time | 2-25 minutes |
| Target Solutes | Lactate, $K^+$, Creatinine, Urea, Myoglobin, Cytokines |
| Lactate Reduction | >40% per batch cycle |
| Filter Type | High-flux polysulfone or cytokine-absorptive membrane |
| Safety | Inline pressure, air trap, auto flow shutoff |

Figure 6:
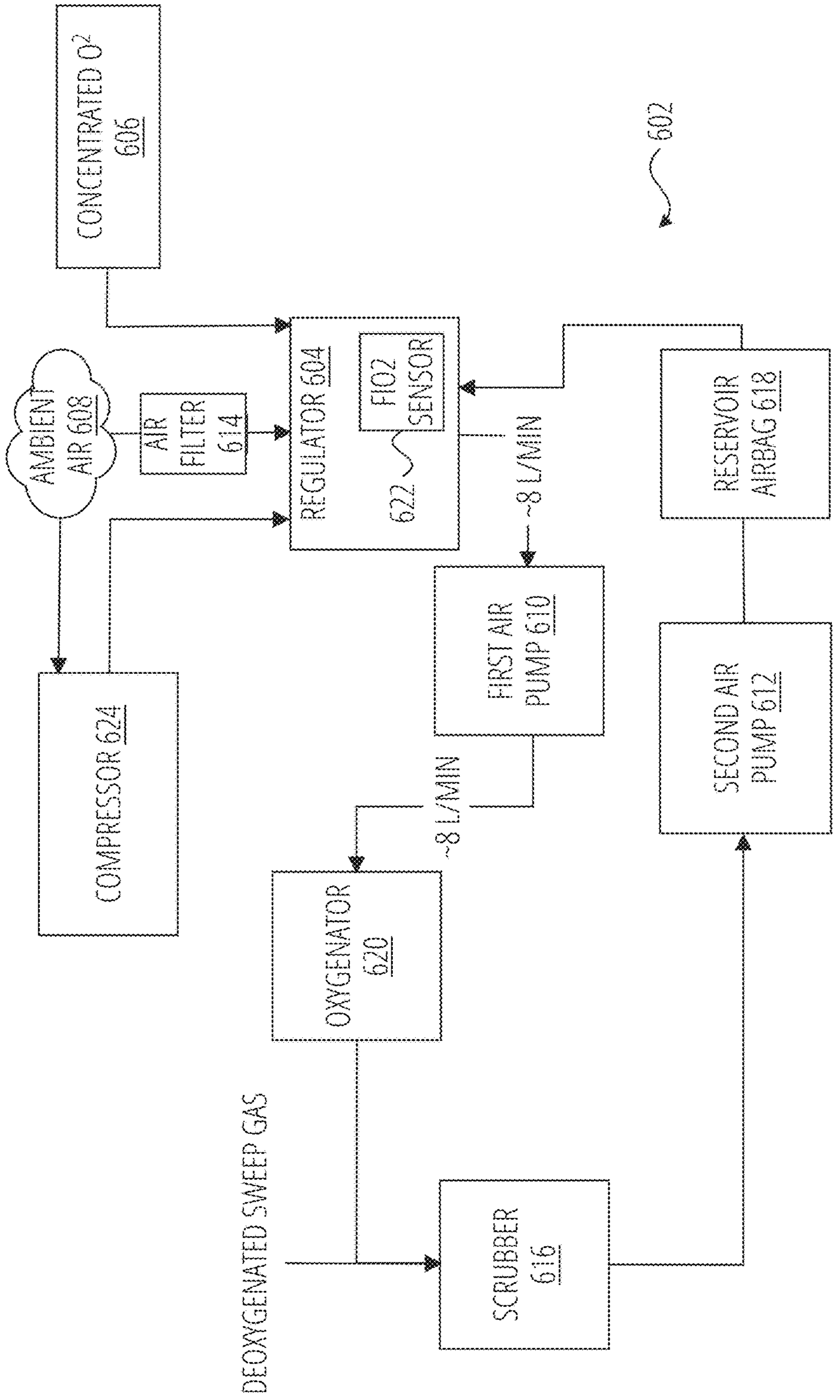
FIG. 6 is a schematic of an air blender for providing a fresh gas line to an oxygenator.

The dialysis filter 596 and the administration of the dialysate from the dialysate source 598 can clear lactate during the extracorporeal blood treatment, such as to promote positive patient outcomes and to mitigate acute kidney injury e.g., due to metabolic derangement that often accompanies traumatic injury. For example, the processing circuitry can facilitate mixing of certain reagents to form or replenish the dialysate. In an example, the system 500B can facilitate formation, mixing, or replenishing of the dialysate at or near the dialysate source 598. For example, a specified portion (e.g., about 1,000 mL) of sterile IsoLyte or saline can be received in an IV bag, and a specified portion (e.g., about 50-100 mL) of Sodium Bicarbonate can be added to thereto to promote buffering capacity. In an example, a specified portion (e.g., about 50 mL) of Dextrose 50% can be further added such as to limit or prevent hypoglycemia and aid diffusion. In an example, a specified portion (e.g., about 2-3 mL) of Heparin can also be added to the IV bag to reduce clotting risk in circuit filters. In an example, the system 500B (e.g., the processing circuitry or any of the pump 530, pump 206, ECMO pump 504, valve 254, etc.) can facilitate counterflowing of the formed or replenished dialysate at the dialysis filter 596 in an opposing direction to that of the blood flow from the blood conditioner 208. For example, at least one of pump 530 or pump 206 can be activated to control blood flow in the fluid circuit at a flow rate of about 1.5 L/min. Here, the blood can repeatedly recirculate from the enclosed bag 30, through the conditioner 208, through the dialysis filter 596, and back toward the enclosed bag 230. The system 500B can receive dialysate from the dialysate source 598 (e.g., via gravity or alternatively or additionally via a motor or pump). As such, the dialysate can flow through the dialysis filter 598 on an opposite side of a membrane of the dialysis filter 598 than that of the flow of blood. In an example, a specified amount of dialysate (e.g., between about 2.5 and 3.5 L of dialysate) can be received via the dialysis filter 596 during counterflow of the dialysate and the blood in the fluid circuit. Such a counter flow of the dialysate from the dialysate source 598 in an opposing direction to and on an opposite side of the dialysis filter membrane than that of the conditioned blood from the fluid circuit can facilitate removal of between ~70-85% of certain small solutes such as urea, potassium, lactate. Such a process can be repeated (e.g., after a specified period between about 20-70 minutes, such as after about 45 minutes) where additional solute removal is desired. FIG. 6 is a schematic showing portions of an air blender 600 for providing a fresh gas line to an oxygenator. For example, the air blender 600 can provide the sweep gas for use in the blood conditioner 208, such as the oxygenator 126 included therein (as depicted in FIG. 1C). The air blender 600 can also provide a sweep gas for the ECMO oxygenator 506 or other components in the system 500A (as depicted in FIG. 5A).

Certain approaches to providing a sweep gas to an oxygenator can involve mixing a supply of compressed ambient air and compressed oxygen (O2). Such an approach can involve a challenge of supplying each type of compressed air, which can be unfeasible in certain mobile, point-of-trauma (or similar onsite hemorrhage control) circumstances. Further, such approaches may not provide for any function of an oxygenator to condition blood from the subject once a store of compressed ambient air or compressed oxygen becomes depleted. The present inventor has recognized the benefit of an air blender that does not necessarily rely on compressed ambient air for supplying a sweep gas to a blood oxygenator.

The air blender 600 can include, use, or be connected to a regulator 604, a first air pump 610, an oxygenator 126, a second air pump 612, a scrubber 616, and a reservoir airbag 618. The air blender 600 can receive compressed or concentrated $O_2$ 606, uncompressed ambient air 608, or both and mix them via the regulator 604 to establish a desired sweep gas. In an example, where the compressed or concentrated $O_2$ 606 is unavailable or has become depleted, the air blender 600 can facilitate production of a sweep gas, including uncompressed ambient air 608, such as for temporary (e.g., less than about 20 minutes) operation of the oxygenator 126.

As described with respect to FIG. 1C, FIG. 2A, FIG. 2B, and FIG. 5A, an extracorporeal blood conditioning device or system can include the oxygenator 126 to condition blood removed from a human subject, e.g., by oxygenation and removal of carbon dioxide. The oxygenator can operate based on a sweep gas, e.g., established within a specified fraction of inspired oxygen (FiO2) and at constant flow rate. Parameters of the sweep gas can be important for maintaining a desired gas exchange with the subject blood during the oxygenation process in the oxygenator 126. In an example, the regulator can include a FiO2 sensor 620 configured to measure the FiO2 of the sweep gas. Data from the FiO2 sensor 620 can be received by an operator or a processing unit (e.g., unit 160 as depicted in FIG. 1C) such as to help control e.g., via activation of one or more valves, the regulator 604 based on the received data. Control of the one or more valves of the regulator 604 can assist in managing a volume mixing proportion of the sweep gas including oxygen 606 and the sweep gas including uncompressed ambient air 608. In an example, the regulator 604 can include a three-way valve, such as can include a solenoid, gate, or other type of valve that can be configured to route a sweep gas including both the compressed or concentrated $O_2$ 606 and the uncompressed ambient air 608 to the oxygenator 126 in such a proportion that provides a desired $FiO_2$. In an example, the data (such as a display of the data via a user interface) from the FIO2 sensor 620 can be used by an operator or the processing unit to help conserve the volume or supply of the relatively more dense compressed or concentrated $O_2$ 606 (e.g., limited compressed oxygen resources), such can be as based on at least in part on an oxygen content of the ambient air. Thus, the FiO2 sensor 620 can monitor and modulate the supply of the compressed or concentrated $O_2$ 606 resource. The regulator 604 can be similarly controlled based at least in part on other sensor data (e.g., data from one or more sensors embedded within or near the reservoir 204, the enclosed flexible bag 230, the pump 206, or any of valves 252, 254, 256, 258, or 259, as depicted in FIG. 2A), such that FiO2 is modulated based on a patient condition or determined physiological need. Further the regulator 604 can be manually controllable (e.g., via a dial or other user interface) such as to establish the specified FiO2 based on a determination from an operator.

In an example, the air blender 600 can include or use an air filter 614 for filtering the ambient air before introduction to the regulator 604. In addition to filtering the ambient air 608, the air filter 614 can help remove water, other liquids, or undesirable particulates. For instance, the air filter 614 can include one or more of activated carbon or HEPA filters for filtering the plausible presence of one or more of undesired chemicals, undesired microorganism, fungi, virus or other bioaerosol.

Optionally, the air blender 600 can include an auxiliary compressor 624 for compressing the ambient air 608 before introduction to the regulator 604. In an example, such auxiliary compression can help compensate for flow rate differences for a supply of compressed $O_2$ 606 and for the supply of ambient air 608. The air filter 614 can be placed before (upstream from) or after (downstream from) the auxiliary compressor 624. Additionally, in an example, the auxiliary compressor 624 can include one or more of an electrically driven compressor, a mechanical crank driven air supply, or any other type of air compressor.

The first air pump 610 and the second air pump 612 can pump the sweep gas to and from oxygenator 126, respectively. For example, the first pump 610, the second pump 612, or both can include or be coupled to a respective airflow sensor for measuring airflow of sweep gas and controlling pump operation to maintain a constant airflow of sweep gas at a constant flow rate between 7 liters per minute (L/min) and 9 L/min. Herein, "constant flow rate" means a flow rate that is selected by an operator or a processing unit and is maintained within a range that does not allow the volume of sweep gas traveling through the oxygenator 126 to vary more than a threshold variability amount, such as more than +/−0.25 L/min. In an example where the constant flow rate is about 8 L/min, an operator or the processing unit determines the air blender 600 needs to push about 1 L/min of the compressed or concentrated $O_2$ 606 (based on the FiO2 concentration measured prior to (e.g., upstream from) the regulator 604 and via the FiO2 Sensor 620), and the regulator 604 the facilitates mixing of the remaining ~7 L/min as ambient air 608.

In an example, one or both of the first air pump 610 and the second air pump 612 can operate as a compressor to compress the blended air such as to increase flow across the oxygenator. For example, the first air pump 612 can produce or use a vacuum to pull blended air from the regulator 604 and toward the oxygenator. The blended air can pass through the oxygenator to oxygenate the blood, the $CO_2$ can be swept off the blood in the oxygenator. In an example, the second air pump 612 can produce or use vacuum to pull used air (e.g., at least partially depleted of $O_2$) out of the oxygenator can facilitate discarding of the $CO_2$ out of the air blender and out of the device or system.

In an example, the air blender 600 can include, use, or be connected with a scrubber 616. The scrubber 616 can receive used (e.g., at least partially deoxygenated) sweep gas from the second air pump 612 and recover a desired constituent, such as remaining $O_2$, from the used sweep gas before discarding the recovered constituent of the sweep gas as exhaust. The scrubber 616 can include or use sodalime or a $CO_2$ or other absorbent. For example, the sodalime can be a solid (e.g., hard granular) or powdered (e.g., fine particulate). The sodalime can include an active constituent selected from group I metals, barium, magnesium, calcium, carbon, copper, iron, cobalt and/or nickel. In an example, the active constituent of sodalime can be NaOH, KOH, Ba(OH) 2, Mg(OH)2, Ca(OH)2, NaOH, KOH, or both. Further the ratio of the active constituent, which can be Na or KOH, can be set or otherwise specified to sufficiently extract $CO_2$ in a removed volume of air. In an example, the ratio of the active constituent of ground sodalime can represent a weight of about 1.1-1.6:1. O2 recovered by the scrubber can be stored in the reservoir bag 618 and eventually introduced back into the regulator 604 as concentrated $O_2$ 606. In an example, the reservoir airbag 618 can house a volume between about 1000 mL of air and about 3000 mL of air, such as about 2000 mL of air. In an example, the scrubber 616 can be configured to facilitate recovery of at least 50% of the remaining oxygen from the at least partially deoxygenated air exiting the second air pump 612, such as recovery of at least 60% of the remaining oxygen, recovery of at least 70% of the remaining oxygen, recovery of at least 80% of the remaining oxygen, or recovery of at least 90% of the remaining oxygen.

In an example, the scrubber 616 can be integrated with the oxygenator 126, for example, as a sealed end cap on an outflow end of the oxygenator. Here, as excess gas exits the oxygenator 126 through a port of the sealed end cap. The gas can pass a recovery sensor arranged to provide an indication of a gas level, such as an amount of oxygen depletion or oxygen saturation, of the sweep gas exiting the oxygenator 126 (e.g., levels of NiO2 and CO2). The gas can be pulled via a vacuum of the second air pump 612 and through the sodalime of the scrubber 616 such that, e.g., water and CO2 can be separated out by the scrubber 616. Recovered oxygen from the scrubber 616 can be propelled via the second air pump 612 through a fluid conduit toward the reservoir bag 618.

Figure 7:
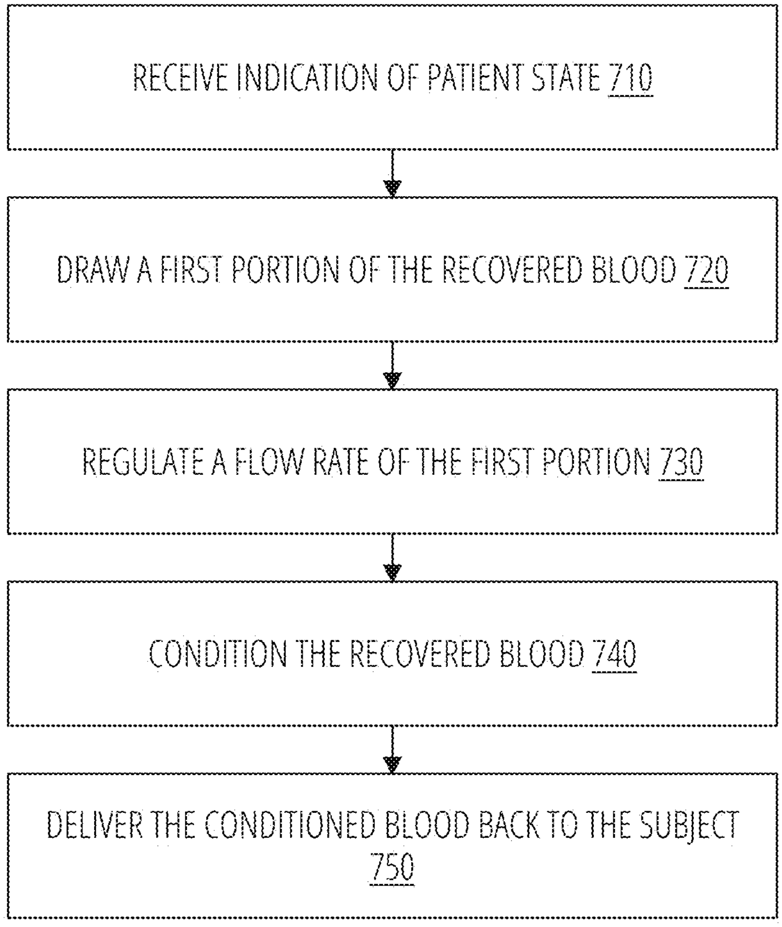
FIG. 7 is a flowchart showing a method for performing extracorporeal blood treatment of recovered blood.

FIG. 7 is a flowchart showing a technique for performing extracorporeal blood treatment of recovered blood. The technique 700 can be implemented using one or more devices or systems described herein, such as the system 100 of FIG. 1A, FIG. 1B, and FIG. 1C, the blood treatment device 250 of FIG. 2A and FIG. 2B, etc.

The technique 700 includes an operation 710 to receive an indication of a patient state including a patient having lost greater than 500 milliliters (mL) of blood. Herein, indications and determinations of blood loss include blood "lost"

into an internal cavity of the patient, such as an internal bleed, and need not be limited to an actual volume of blood removed from the patient. For example, a patient losing greater than 500 mL of blood can indicate the patient is a trauma patient in need of intervention to avoid hemorrhagic shock. For example, operation 720 through operation 750 can be performed conditional upon a determination or receipt of indication that the patient state would otherwise qualify for a massive transfusion protocol.

The technique 700 includes an operation 720 to draw a first portion of the recovered blood from a body cavity of the subject and into a reservoir. For example, a trocar can be placed at the body cavity and connected via a tubing to the reservoir. In an example, the technique can include cutting or enlarging a hole at or near the body cavity to better facilitate access to an internal bleed of the subject. In an example, the reservoir can be sealed relative to an external ambient environment. Here, a negative internal pressure can be applied to the reservoir relative to the external ambient environment, e.g., via a source of suction. The source of suction can be selectively applied or disabled such as to facilitate drainage out of the reservoir when a reservoir valve is opened.

The technique 700 includes an operation 730 to regulate a flow rate of the first portion of the recovered blood. The flow rate can be maintained or regulated at a value greater than 200 milliliters per minute (mL/min). For example, regulating the flow rate can include modulating an inline pump, e.g., between about 1 liter per minute (L/min) and about 10 L/min. In an example, regulating the flow rate can include modifying a flow rate based on an established or adjusted blood treatment operating mode.

The technique 700 includes an operation 730 to condition the recovered blood. For example, conditioning the recovered blood can include reoxygenating hemoglobin (Hb) or removing carbon dioxide ($CO^2$) from the recovered blood. Conditioning the recovered blood can also include controlling a temperature of the recovered blood. In an example, a temperature of the recovered blood can be controlled, e.g., heated, before reoxygenating Hb. In an example, regulating the temperature can include modifying a temperature based on an established or adjusted blood treatment operating mode.

The technique 700 includes an operation 740 to monitor an indication of blood state over time. For example, the indication of blood state can include monitoring a blood volume recovered from the patient over time. The indication of blood state can also include an indication of blood lactate concentration over time, e.g., received from a blood lactate sensor. The indication of blood state can also include an indication of arterial blood gas (ABG) over time, e.g., received from an ABG sensor.

The technique 700 includes an operation 750 to deliver the conditioned, recovered blood back to the subject at least intravenously. The technique 700, in certain blood treatment operating modes, can include delivering the conditioned, recovered blood back to the subject both intravenously and intra-arterially. In an example, an anticoagulant can be administered to the subject prior to the drawing the first portion of the recovered blood from the body cavity of the subject into the reservoir. For example, the blood thinning agent can include heparin, bivalirudin, or argatroban.

In an example, the technique 700 can include establishing or adjusting a blood conditioner operating parameter based on blood state. For example, the blood conditioner operating parameter can be at least one operating parameter of an oxygenator or a temperature regulator. The blood conditioner operating parameter can be established or adjusted based on a monitored indication of blood lactate concentration of the subject over time.

In an example, the technique 700 can include establishing or adjusting a blood treatment operating mode, determined at least in part based on the monitored indication of blood state over time. For example, the blood treatment operating mode can be selected between an assist mode, an acidosis mode, and a controlled preservation mode. For example, in the assist mode, blood can be regulated at a first temperature and reoxygenated blood can be delivered intravenously back to the subject after the reoxygenating Hb. In the acidosis mode, the flow rate of the first portion of the recovered blood can be increased and a second portion of the recovered blood can be received via intravenous cannulation of the subject. In an example, the flow rate of both the first portion and the second portion of the recovered blood can be regulated via the same pump. In the controlled preservation mode, a biological function of the subject can be slowed to help preserve organ tissue. The controlled preservation mode can include cooling the recovered blood toward a second temperature lower than the first temperature before delivering the cooled blood back intra-arterially to the subject. For example, in the controlled preservation mode, an internal body temperature can of the patient can be induced to a temperature between about 10° C. and 20° C. Also, in the controlled preservation mode, controlled hypothermic arrest can be induced in the patient. In an example, the assist mode, the acidosis mode, and the controlled preservation mode of blood treatment can be performed sequentially, such as to escalate a blood treatment protocol based on a declining patient condition. For example, the declining patient condition can be determined based on the measured indication of blood state, such a monitored indication of blood lactate concentration.

Figure 8:
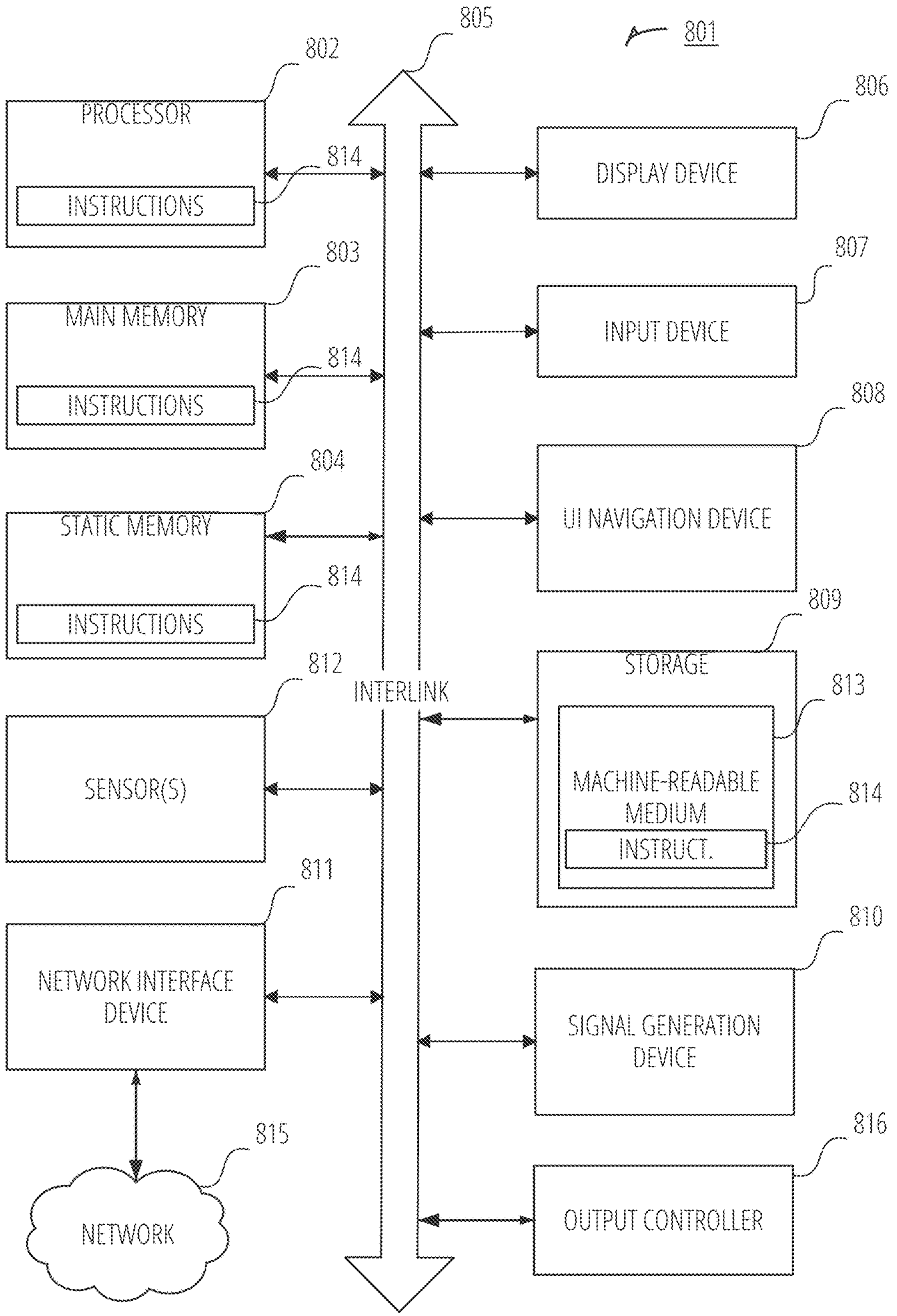
FIG. 8 is a block diagram of an example of a machine.

FIG. 8 illustrates generally an example of a block diagram of a machine 801 upon which any one or more of the techniques (e.g., methodologies) discussed herein may perform in accordance with some examples. In alternative embodiments, the machine 801 may operate as a standalone device or may be connected (e.g., networked) to other machines. In a networked deployment, the machine 801 may operate in the capacity of a server machine, a client machine, or both in server-client network environments. In an example, the machine 801 may act as a peer machine in peer-to-peer (P2P) (or other distributed) network environment. The machine 801 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. In this example, the execution units may be a member of more than one module. For example, under operation, the execution units may be configured by a first set of instructions to implement a first module at one point in time and reconfigured by a second set of instructions to implement a second module.

Machine (e.g., computer system) 801 may include a hardware processor 802 (e.g., a central processing unit (CPU), a graphics processing unit (GPU), a hardware processor core, or any combination thereof), a main memory 803 and a static memory 804, some or all of which may communicate with each other via an interlink (e.g., bus) 805. The machine 801 may further include a display unit 806, an alphanumeric input device 807 (e.g., a keyboard), and a user interface (UI) navigation device 808 (e.g., a mouse). In an example, the display unit 806, alphanumeric input device 807 and UI navigation device 808 may be a touch screen display. The machine 801 may additionally include a storage device (e.g., drive unit) 809, a signal generation device 810 (e.g., a speaker), a network interface device 811, and one or more sensors 812, such as a global positioning system (GPS) sensor, compass, accelerometer, or other sensor. The machine 801 may include an output controller 816, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 809 may include a machine readable medium 813 that is non-transitory on which is stored one or more sets of data structures or instructions 814 (e.g., software) embodying or utilized by any one or more of the techniques or functions described herein. The instructions 814 may also reside, completely or at least partially, within the main memory 803, within static memory 804, or within the hardware processor 802 during execution thereof by the machine 801. In an example, one or any combination of the hardware processor 802, the main memory 803, the static memory 804, or the storage device 809 may constitute machine readable media.

While the machine readable medium 813 is illustrated as a single medium, the term "machine readable medium" may include a single medium or multiple media (e.g., a centralized or distributed database, or associated caches and servers) configured to store the one or more instructions 814.

The term "machine readable medium" may include any medium that is capable of storing, encoding, or carrying instructions for execution by the machine 801 and that cause the machine 801 to perform any one or more of the techniques of the present disclosure, or that is capable of storing, encoding or carrying data structures used by or associated with such instructions. Non-limiting machine-readable medium examples may include solid-state memories, and optical and magnetic media. Specific examples of machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 814 may further be transmitted or received over a communications network 815 using a transmission medium via the network interface device 811 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 702.16 family of standards known as WiMax®), IEEE 702.15.4 family of standards, peer-to-peer (P2P) networks, among others. In an example, the network interface device 811 may include one or more physical jacks (e.g., Ethernet, coaxial, or phone jacks) or one or more antennas to connect to the communications network 815. In an example, the network interface device 811 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 801, and includes digital or analog communications signals or other intangible medium to facilitate communication of such software.

The above Detailed Description can include references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that can include elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" can include "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that can include elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A portable rapid autotransfusion system for point-of-injury or similar onsite portable hemorrhage control in a trauma patient, the system comprising:

a fluid reservoir, at least partially open to air in an ambient environment about the system, the fluid reservoir configured for recovering a first portion of patient blood, from an extravascular space of a patient into which the first portion of the patient blood has hemorrhaged; and an enclosed flexible bag, fluidly connected to an outlet of the fluid reservoir configured for permitting outgassing of gas from the first portion of patient blood out of the enclosed flexible bag;

a first conditioning fluid circuit, including or fluidly connected to the enclosed flexible bag and fluidly sealed from the air in the ambient environment about the system, the first conditioning fluid circuit including:

a first blood conditioner including a first oxygenator, the first blood conditioner configured for conditioning the first portion of patient blood including oxygenating, and removing carbon dioxide ($CO^2$) from the first portion of patient blood; and a heat exchanger for controlling, concurrently with the conditioning, a temperature of the first portion of patient blood; and a second conditioning fluid circuit, fluidly connected to an outlet of the first blood conditioner, the second conditioning fluid circuit including a second oxygenator;

wherein, concurrent with recovering patient blood from the patient, the second conditioning circuit is configured to return conditioned blood back to the patient intravenously via a fluid outlet of the second conditioning fluid circuit.

2. The system of claim 1, wherein the system is configured to recirculate the first portion of patient blood within the first conditioning fluid circuit, before passage of the first portion of patient blood to the second conditioning fluid circuit, the recirculation comprising passing the blood through a filter or gas exchanger configured to further remove carbon dioxide or particulates from the first portion of patient blood.

3. The system of claim 1, wherein the second fluid circuit includes at least one of a valve or a pressure source or a magnetically levitated pump arranged between a fluid outlet of the first blood conditioner and the second oxygenator.

4. The system of claim 1, wherein the second conditioning fluid circuit is an extracorporeal membrane oxygenation (ECMO) device.

5. The system of claim 1, wherein the enclosed flexible bag is formed of a membrane is semipermeable configured to permit gas exchange while not permitting blood to permeate from the enclosed flexible bag.

6. The system of claim 1, comprising a conduit disposed between the fluid reservoir and the enclosed flexible bag, the conduit arranged to allow the gas outgassed from the first portion of patient blood out of the enclosed flexible bag to be purged into the fluid reservoir.

7. The system of claim 1, comprising a sensor for monitoring, following the conditioning, at least one of blood lactate or arterial blood gas (ABG) of the first portion of patient blood and establish or adjust at least one parameter of the conditioning or the controlling a temperature of the first portion of blood.

8. The system of claim 1, wherein the second conditioning circuit is configured to concurrently receive each of:

the first portion of patient blood, via the outlet of the first blood conditioner of the first conditioning circuit; and a second portion of patient blood, via an inlet of the second conditioning circuit configured to receive the second portion of patient blood intravenously from the patient.

9. The system of claim 8, wherein the second conditioning circuit includes an inline fluid pump configured to draw at least one of the first portion of patient blood or the second portion of patient blood into the second conditioning circuit.

10. A method for point-of-injury or similar onsite portable hemorrhage control in a trauma patient, the method comprising:

recovering a first portion of patient blood, from an extravascular space of a patient into which the first portion of the patient blood has hemorrhaged via a fluid reservoir, wherein the fluid reservoir is at least partially open to air in an ambient environment;

outgassing air from the first portion of patient blood, within an enclosed flexible bag fluid connected to an outlet of the fluid reservoir, the outgassing including impeding blood from permeating through the enclosed flexible bag;

conditioning the first portion of patient blood via a first conditioning fluid circuit fluidly connected to the enclosed flexible bag and fluidly sealed from air from an external ambient environment, the conditioning including oxygenating the first portion of patient blood via a first oxygenator and controlling a temperature of the first portion of patient blood; and conditioning the first portion of patient blood via a second conditioning fluid circuit, following the conditioning via the first conditioning fluid circuit, including oxygenating the first portion of blood via a second oxygenator; and returning, concurrent with recovering patient blood from the patient, conditioned blood back to the patient intravenously via a fluid outlet of the second conditioning fluid circuit.

11. The method of claim 10, comprising recirculating the first portion of patient blood within the first conditioning fluid circuit, before passage of the first portion of patient blood to the second conditioning fluid circuit, the recirculation comprising passing the blood through a filter or gas exchanger configured to further remove carbon dioxide or particulates from the first portion of patient blood.

12. The method of claim 10, wherein the conditioning via the second conditioning fluid circuit includes extracorporeal membrane oxygenation (ECMO).

13. The method of claim 10, comprising permitting gas exchange while not inhibiting blood from permeating from the enclosed flexible bag, via a semipermeable membrane of the enclosed flexible bag.

14. The method of claim 10, comprising directing the gas outgassed from the first portion of patient blood out of the enclosed flexible bag, toward the fluid reservoir, via a conduit disposed between the fluid reservoir and the enclosed flexible bag.

15. The method of claim 10, comprising:

monitoring, following the conditioning, at least one of blood lactate or arterial blood gas (ABG) of the first portion of patient blood; and establishing or adjusting at least one parameter of the conditioning or the controlling a temperature of the first portion of blood.

16. The method of claim 10, comprising recovering a second portion of patient blood, concurrently with the recovering the first portion of patient blood, the recovering the second portion of patient blood including receiving the second portion of patient blood at an inlet of the second conditioning circuit.

17. The method of claim 16, comprising intravenously cannulating the patient to receive the second portion of patient blood at the inlet of the second conditioning circuit.

18. The method of claim 16, comprising drawing, into the second conditioning circuit at least one of the first portion of patient blood or the second portion of patient blood, via an inline fluid pump included in the second conditioning circuit.

* * * * *